(12) United States Patent
Shizukuishi

(10) Patent No.: US 11,457,882 B2
(45) Date of Patent: Oct. 4, 2022

(54) IMAGING APPARATUS AND DRIVING METHOD THEREOF

(71) Applicant: Makoto Shizukuishi, Sendai (JP)

(72) Inventor: Makoto Shizukuishi, Sendai (JP)

( * ) Notice: Subject to any disclaimer, the term of this patent is extended or adjusted under 35 U.S.C. 154(b) by 91 days.

(21) Appl. No.: 17/144,710

(22) Filed: Jan. 8, 2021

(65) Prior Publication Data

US 2021/0153825 A1 May 27, 2021

Related U.S. Application Data

(63) Continuation of application No. PCT/JP2019/050276, filed on Dec. 23, 2019.

(30) Foreign Application Priority Data

Dec. 26, 2018 (JP) .............................. JP2018-242594
Sep. 11, 2019 (JP) .............................. JP2019-165058

(51) Int. Cl.
*A61B 6/00* (2006.01)
*A61B 6/03* (2006.01)
(Continued)

(52) U.S. Cl.
CPC ............ *A61B 6/4435* (2013.01); *A61B 6/032* (2013.01); *A61B 6/0407* (2013.01);
(Continued)

(58) Field of Classification Search
CPC ..... A61B 6/4435; A61B 6/032; A61B 6/0407; A61B 6/4241; A61B 6/461;
(Continued)

(56) References Cited

U.S. PATENT DOCUMENTS

| | | | |
|---|---|---|---|
| 4,912,735 A | 3/1990 | Beer |
| 4,928,283 A | 5/1990 | Gordon |

(Continued)

FOREIGN PATENT DOCUMENTS

| | | |
|---|---|---|
| CN | 1689524 A | 11/2005 |
| DE | 102004019599 A1 | 11/2005 |

(Continued)

OTHER PUBLICATIONS

International Search Report dated Mar. 24, 2020 for corresponding International Application No. PCT/JP2019/050276.

*Primary Examiner* — Courtney D Thomas
(74) *Attorney, Agent, or Firm* — Harness, Dickey & Pierce, P.L.C.

(57) ABSTRACT

A computed tomographic (CT) system includes a gantry having a rotating part including a light source, a light source drive control circuit, a rechargeable battery, and a rotating part interface. The gantry includes a detector, a detector control and signal processing circuit, and an image memory. The rotating part may rotate around a central axis. The CT system includes a gantry table on which the gantry is mounted and which includes a host interface. The CT system includes a motor that may cause the gantry to move within a gantry moving range, and a control unit that may process and display image data obtained from the gantry. The rotating part interface may face the host interface, such that the rotating part and host interfaces are configured to be electrically connected with each other, based on the gantry being at a predetermined position within the gantry moving range.

20 Claims, 10 Drawing Sheets

(51) Int. Cl.
  *A61B 6/04* (2006.01)
  *G16H 40/67* (2018.01)
(52) U.S. Cl.
  CPC ............ *A61B 6/4241* (2013.01); *A61B 6/461* (2013.01); *G16H 40/67* (2018.01); *A61B 2562/046* (2013.01)
(58) Field of Classification Search
  CPC ... A61B 2562/046; A61B 6/4014; A61B 6/56; G16H 30/20; G16H 40/63
  See application file for complete search history.

(56) References Cited

U.S. PATENT DOCUMENTS

| | | | |
|---|---|---|---|
| 9,700,272 B2 | 7/2017 | Gregerson | |
| 9,808,159 B2 | 11/2017 | Shizukuishi | |
| 9,943,275 B2 | 4/2018 | Shizukuishi | |
| 9,962,132 B2 | 5/2018 | Gregerson et al. | |
| 10,151,810 B2 | 12/2018 | Gregerson et al. | |
| 2003/0095635 A1 | 5/2003 | Moritake et al. | |
| 2005/0238137 A1 | 10/2005 | Popescu | |
| 2009/0200470 A1 | 8/2009 | Ohta et al. | |
| 2012/0256099 A1 | 10/2012 | Gregerson et al. | |
| 2014/0079191 A1* | 3/2014 | Daum ................ | A61B 6/4405 378/198 |
| 2014/0139215 A1 | 5/2014 | Gregerson et al. | |
| 2017/0360387 A1 | 12/2017 | Gregerson et al. | |

FOREIGN PATENT DOCUMENTS

| | | |
|---|---|---|
| JP | S61-244330 A | 10/1986 |
| JP | H02-224746 A | 9/1990 |
| JP | H02-503282 A | 10/1990 |
| JP | H04-22100 A | 1/1992 |
| JP | H04-335147 A | 11/1992 |
| JP | H07-204192 A | 8/1995 |
| JP | H08-56939 A | 3/1996 |
| JP | H08-336521 A | 12/1996 |
| JP | H10-66690 A | 3/1998 |
| JP | H11-70102 A | 3/1999 |
| JP | H11-188029 A | 7/1999 |
| JP | 2001-258873 A | 9/2001 |
| JP | 2001-258874 A | 9/2001 |
| JP | 2002-34967 A | 2/2002 |
| JP | 2002-78703 A | 3/2002 |
| JP | 2003-153889 A | 5/2003 |
| JP | 2003-169792 A | 6/2003 |
| JP | 2003-180674 A | 7/2003 |
| JP | 2003-288853 A | 10/2003 |
| JP | 2005-143991 A | 6/2005 |
| JP | 2005-516343 A | 6/2005 |
| JP | 2005-305165 A | 11/2005 |
| JP | 2006-68534 A | 3/2006 |
| JP | 2009-183559 A | 8/2009 |
| JP | 2009-219585 A | 10/2009 |
| JP | 2011-5244 A | 1/2011 |
| JP | 2012-138867 A | 7/2012 |
| JP | 5027339 B1 | 9/2012 |
| JP | 2012-245359 A | 12/2012 |
| JP | 5424371 B1 | 2/2014 |
| JP | 2015-217137 A | 12/2015 |
| JP | 5970641 B2 | 8/2016 |
| JP | 6586550 B1 | 10/2019 |
| WO | WO-1989/008269 A1 | 9/1989 |
| WO | WO-2003/063195 A1 | 7/2003 |
| WO | WO-2012/139014 A2 | 10/2012 |
| WO | WO-2013/188617 A1 | 12/2013 |

* cited by examiner

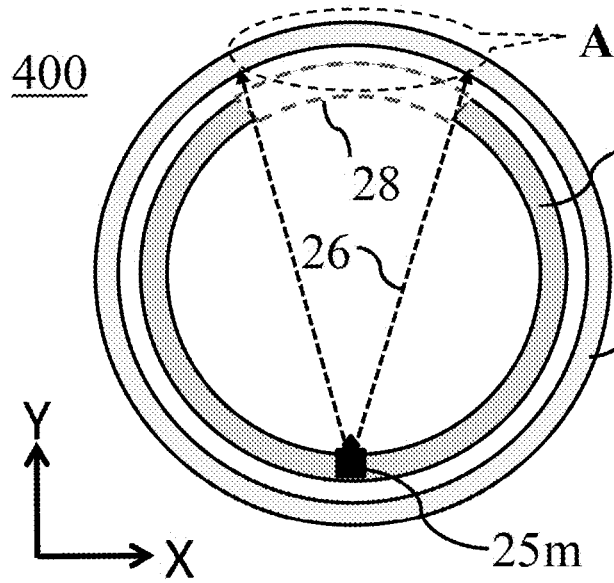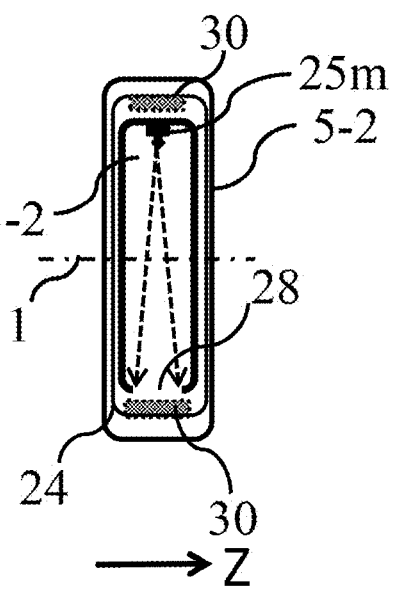
FIG.5(a)  FIG.5(b)
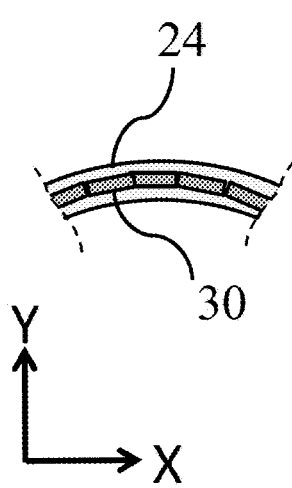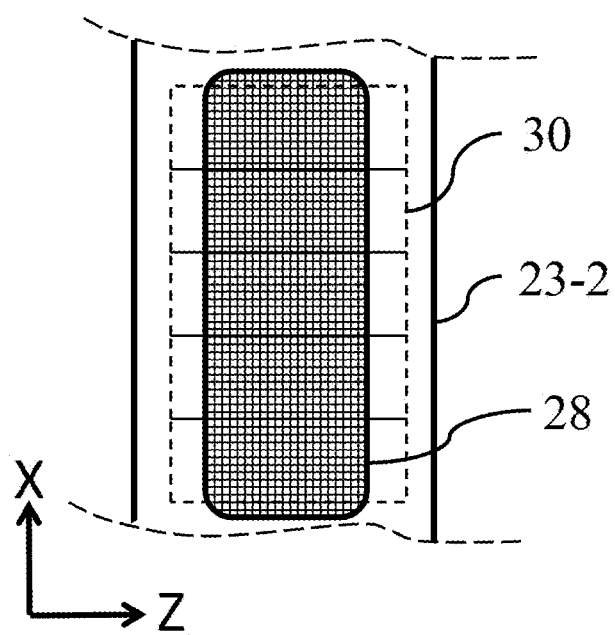
FIG.5(c)  FIG.5(d)

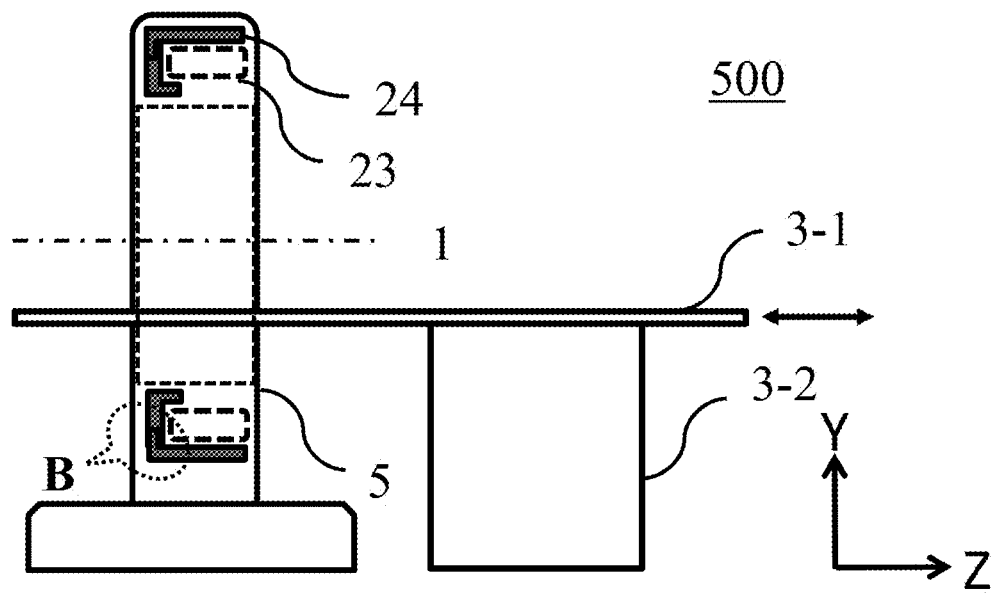
FIG.7(a)
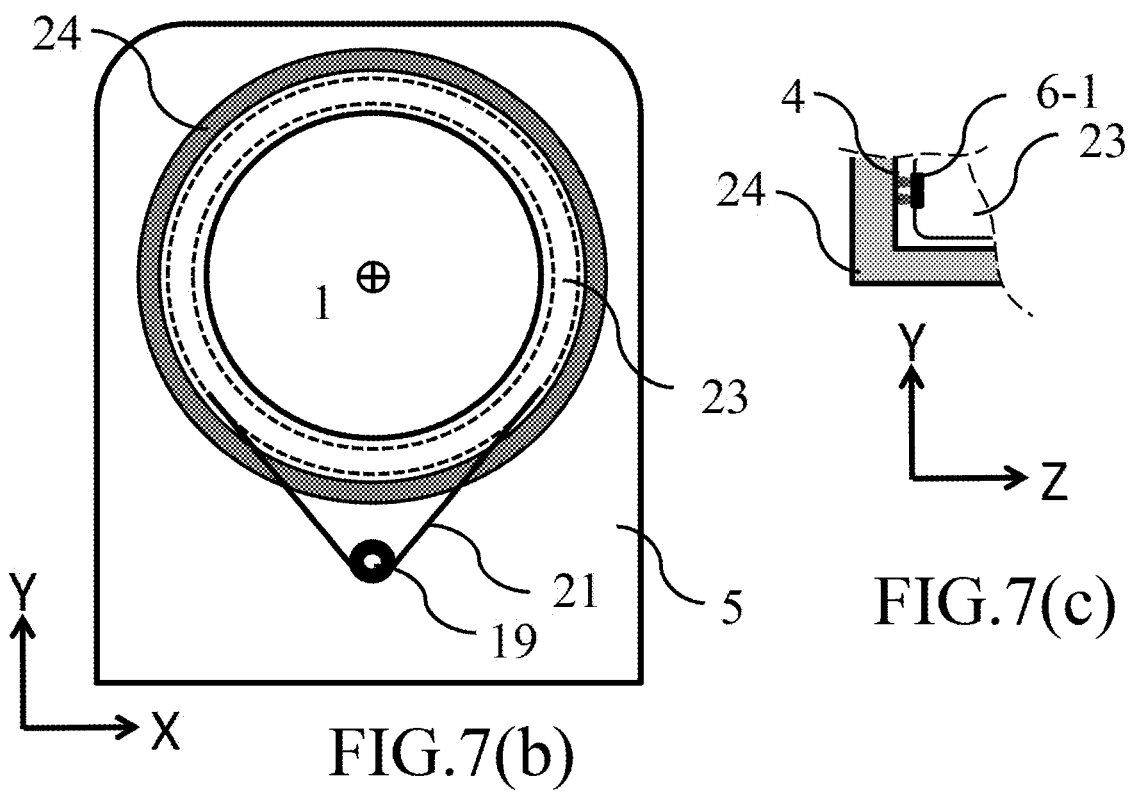
FIG.7(b)
FIG.7(c)

IMAGING APPARATUS AND DRIVING METHOD THEREOF

CROSS-REFERENCE TO RELATED APPLICATIONS

This application is a Continuation of PCT/JP2019/050276 filed on Dec. 23, 2019, which claims priority to Japanese Patent Application No. 2018-242594 filed on Dec. 26, 2018, in the Japanese Patent Office (JPO), and Japanese Patent Application No. 2019-165058 filed on Sep. 11, 2019, in the JPO, the entire contents of each of which are incorporated herein by reference.

BACKGROUND

1. Technical Field

Example embodiments relate to an imaging apparatus such as a computer tomographic (CT) system and a driving method thereof enabling high spatial, timing and energy resolution with smaller form factor and lower power consumption.

2. Related Art

An imaging apparatus, for example, an X-ray computed tomographic (CT) system comprises a gantry including a rotating part that rotates around an imaging target, a bed on which a subject is placed so as to pass through the inside of the gantry in the direction of the central axis of the rotation, a moving bed supporting member, and a slip ring around the rotating part enabling an electrical connection with an operation and monitoring console which reconstructs the subject image using the image data transferred via the slip ring. Inside the rotating part, a detector composed of a group of a large number of image pickup elements, a circuit board for processing signals from the detector, an X-ray generating part at a position facing each other across an imaging object such as a subject, cooling fan, and a high-voltage power supply circuit are incorporated. A conventional CT system is a large, heavy, and expensive image diagnostic equipment. In addition to the costs of the building where the CT system is installed including the cost of a large power supply and air conditioning systems, also maintenance cost to keep the CT system with optimal performance and conditions at all times cause a heavy financial burden.

SUMMARY

Some example embodiments provide X-ray CT systems having reduced size and cost, which will contribute to the health maintenance of people all over the world. Particularly, it is desired to detect cancers and other diseases in their early stages and reduce the increasing medical expenses. Even in developing countries, other remote areas and depopulated areas, it is necessary to provide the latest and highest level of medical services to eliminate the medical disparities resulting from natural disasters and regional conflicts. Various unsolved technical problems, such as increased size and cost of a CT system, still remain and an effective breakthrough has not been found yet. One of the factors that hinder the downsizing of conventional CT system may be the difficulty to reduce the size and weight of the gantry. The inner diameter of the rotating part in the gantry is required to be an inner diameter dimension such that a human body can move and pass in the body axis direction with a margin, for example, an inner diameter of 80 cm or more. The outer diameter of the gantry usually exceeds 100 cm because the X-ray source and detector parts must be installed. Generally, a detector, a detector signal processing circuit, an X-ray source, an X-ray source drive control circuit, and cooling fan need to rotate inside the gantry. However, the X-ray source, the X-ray source drive control circuit, the air-cooling fan, for example, are heavy weight. Therefore, it should be necessary to suppress vibrations and noises associated with the rotation and to minimize adverse effects on the entire system caused by the inertial moment of the heavy components rotating at a speed of 1 to 2 revolutions per second on a circle with a diameter of 80 cm or more. Furthermore, in order to move the subject in the body axis direction, it is necessary to move the bed on which the subject is placed forward or backward at a predetermined speed. Considering the variety of subjects and their weight range like several kilograms to 200 kilograms, the bed moving means also needs to ensure robustness capable of covering such a weight range and stable movement of the bed. As a result, such a conventional CT system is prevented from being used on the bedside of a patient or during surgery. In addition, it is difficult to realize a small medical examination vehicle equipped with a CT system.

The detector or the like rotates inside the gantry around the body axis direction at a speed of about 1 to 2 revolutions per second. In order to supply power or read out an output signal from a detector or the like, transmission and reception of a signal, or transmission or reception of power is performed by a mechanical contact means called a slip ring. For the electrical connection by the slip ring, it is necessary to keep the rotation speed low and to reduce the number of output signal lines from the detector. In order to reduce the number of signal lines, serialization of the parallel signal read through the slip ring is adopted. However, when a large amount of image data is serially transmitted, the transmission frequency rises, and then it becomes necessary to develop some custom semiconductor elements such as a high-speed line buffer element, for example. With increase in the transmission frequency, more power consumption and heat generation cannot be avoided. In recent years, the slice width is being widened so that the wide area can be exposed by one-time X-ray pulse irradiation. As a result, in addition to increasing the weight of the gantry, it also needs to increase the size of the X-ray generator. The light receiving area (or the number of slices) in the body axis direction is expanded, which increases the light receiving area of the detector used or the total number of pixels requiring further increases the speed and the capacity of data transmission and high-speed real-time recording. A data processing speed exceeding 1 gigabyte/second is required when the number of slices is 64, for example. In order to record a large amount of data in real time at high speed, it is necessary to use a plurality of hard disks such as RAID (Redundant Arrays of Independent Disks) in combination. In addition to the realization of such high-speed, large-volume data processing, transmission and recording, it is also a problem to be solved by at least one example embodiment of the inventive concepts to reduce the radiation exposure dose of the subject.

The electric power feeding to the X-ray source or the like may cause a problem. Increasing the slice width, the X-ray source increases in size and the amount of current supplied to the X-ray source drive circuit and a high-voltage generation circuit has tended to increase as an X-ray tube current increases. Therefore, the slip ring needs to flow a large amount of current by sliding the brush on the slip ring, which may cause heat generation and seizure on the contact surface. Therefore, maintenance such as surface polishing of the slip ring and brush electrode or regular replacement of these parts are required. For the CT system installation, new design specifications on the building, floor strength, air conditioning equipment and their dedicated power supply system may be reconsidered. The cost of introducing a CT system is not only the installation cost of the CT system itself, but also the cost required for the building including the air conditioning and power supply system, or regular maintenance cost of the temperature and humidity management around the system or the entire building throughout the year. In the case of use outdoor or at a remote location, a large-capacity and stable commercial power for the CT system should be provided, however it may be difficult for a private power generator or a battery to supply enough electric power to the CT system. Therefore, we may need to use sunlight or other natural energy fully or partially in addition to the significant reduction of the power consumption and the energy loss of the CT system. Problems in the CT system to be solved are the reduction of its size, weight, power consumption, and the periodic maintenance load as well as enabling the CT system to be used hybridlike for multiple purposes.

An image pickup apparatus according to at least one example embodiment of the inventive concepts, for example, a CT system has a gantry having a rotating part that rotates about a body axis direction, a gantry table on which the gantry is placed, a control part for processing and displaying image data obtained from the gantry, and an operating part of the CT system. In addition, the CT system has a drive means for moving the gantry in the direction of the central axis. Further, the rotating part has a light source, a light source drive and control circuit, a rechargeable battery (also referred to herein interchangeably as a secondary battery, such as a lithium ion battery) for driving these circuits, and the rotating part interface. The gantry table has a host interface, and the rotating part interface and the host interface are face to face at a predetermined position within the range of the gantry movement. Preferably, the predetermined position is at the end of the gantry moving range. Or the rotating part interface and the host interface are close to each other and face to face in the vertical direction. Alternatively, the rotating part interface and the host interface are close to each other and face to face in the central axis direction. The rotating part interface and the host interface are mechanically contacted to be electrically connected at a predetermined position. Alternatively, the rotating part interface and the host interface are close to each other at a predetermined position and are electrically connected to each other in a contactless manner by an interaction of an electromagnetic field. Further, a driving means for moving the gantry in the central axis direction is provided inside the gantry. Further, a drive motor for rotating the rotating part is provided inside the gantry.

A cradle is provided at a predetermined position above the gantry table, and a host interface is located at the cradle. Further, the cradle has a test probe used for testing or calibrating the rotating part, or a holding means for holding a correlation sample. Preferably, the cradle has a holding mechanism for holding and fixing the rotating part at the predetermined position, or a cooling mechanism for cooling the rotating part. A CT system comprises a gantry having a rotating part, which rotates about the body or central axis direction, incorporates a detector, a detector control and signal processing circuit for driving the detector and processing an output signal of the detector, and an image memory for recording the output signal of the detector. A CT system comprises a bed apparatus for introducing a subject into a gantry, and a control part for processing and displaying image data obtained from the gantry, wherein a rotating part includes a light source, a light source drive control circuit, and a rechargeable battery. The CT system has a structure in which the rotating part has a rotating part interface and a fixed part around the rotating part having a host interface being face to face with the rotating part interface.

Inside the rotating part of a CT system, in addition to the light source and the light source drive control circuit for driving the light source, at least a detector is placed at a position facing the light source to sandwich the central axis therebetween. Further, a detector drive and its output signal processing circuit, an image memory for recording the output signal of the detector, and a rechargeable battery for driving these components are incorporated inside the rotating part. Preferably, a lithium ion battery is used as the rechargeable battery. As the image memory, a large-capacity semiconductor memory, for example, such as a dynamic random-access memory (DRAM) or a non-volatile memory like a NAND flash memory may be used. The light source is an X-ray light source or a near infrared (NIR) light source, for example. Preferably, the light source is an X-ray light source which employs a carbon nanostructure for an electron beam generating part. The detector is preferably a silicon-based semiconductor sensor, and an analog to digital (AD) conversion circuit is also formed on the silicon-based semiconductor sensor. Preferably, the detector may be a photomultiplier tube type sensor, an avalanche photodiode (APD) type sensor, or a photon counting type sensor. Preferably, the radiation shielding optical fiber plate may be provided on the detector, or the radiation scintillator may be further laminated on the radiation shielding optical fiber plate. Further, the CT system has a wireless interface on the gantry, on the gantry table, on the bed, or on the cradle in order to transmit and receive a control signal to control the movement of the gantry or the bed in the body axis direction, and to operate the imaging process inside the gantry. A CT system may have the detector being arranged over the entire inner circumference of the fixed part, and the rotating part may have an opening at the opposite side of the light source to sandwich the rotating central axis, the light emitted from the light source is allowed to pass through the opening.

A plurality of induction coils are arranged along the annular part of the rotating part, and permanent magnets are arranged along the fixed part of the gantry that surrounds the rotating part. A CT system may have an energy recovery brake circuit in the rotating part, where an electromotive force in the induction coils, induced by the moment of inertia about the rotating part, may be converted into the electric energy and stored. Alternatively, a plurality of induction coils are arranged along the circumference of the fixed part inside the gantry surrounding the circumference of the rotating part, and the permanent magnets are arranged along the circumference of the rotating part so that the N poles and the S poles are alternately placed. Preferably, an energy recovery brake circuit for converting the kinetic energy of the rotating part into an electric energy is connected to the induction coils. An electric double layer capacitor may be provided in the energy recovery brake circuit. Further, the CT system has a wireless interface on the gantry side, on the gantry table side, or on the cradle side in order to transmit and receive a control signal to control the movement of the gantry in the body axis direction, and to operate the imaging process inside the gantry. Further, a second gantry is added on the gantry table. A holding means for placing and holding a subject or an object to be measured is integrally formed with the gantry table. A guide rail for assisting the movement of the gantry in the body axis direction is provided on the gantry table. Further, a protective cover for preventing the subject or the object to be measured from meeting the moving gantry is provided on the gantry table along the moving direction of the gantry. A light source, a detector, an image memory for recording the output signal of the detector, or a secondary battery inside the rotating part rotating around the body axis may be a cartridge form. Further, the rotating part has a cartridge receiving space having an opening for inserting or removing the cartridge in the direction of the central axis in the rotating part. The number of cartridges receiving spaces are set to be larger than the number of cartridges to be inserted.

A method of driving the CT system includes steps, the gantry starts to move in the direction of the central axis of the gantry, then the optical signal transmitted through the subject is converted into an electric signal by the detector and recorded the electric signal into the image memory while the rotating part is rotating. Then, the movement of the gantry in the direction of the central axis is stopped at a predetermined position, and the electric signal recorded in the image memory is read out from the rotating part interface through the host interface. A method of driving the CT system includes steps, the gantry starts to move in the central axis direction of the gantry, the light emitted from the light source is converted into an electric signal by the detector and recorded the electrical signal into the image memory while the rotating part is rotating. Then, in the step of decelerating the rotation of the rotating part, the counter electromotive force generated in the induction coil charges into the rechargeable battery or the capacitor via the energy recovery brake circuit. Alternatively, the gantry of the CT system stops its movement in the direction of the central axis at a predetermined position, and then the rechargeable battery is supplied power charged from the host interface via the rotating part interface.

As is discussed in greater detail below, a CT system equipped with a detector array having low noise and low power consumption can be realized using a CMOS type sensor in which a signal processing circuit is integrated on-chip or by laminating an element on the sensor. In addition, since an extremely sensitive detector can be used to reduce the amount of the radiation exposure to the subject. Further, the reduction in the size and weight of the CT system and the reduction in power consumption can significantly reduce the space for installing the CT system, the construction of the building and the power supply, the air conditioning equipment, and the maintenance cost. Further, the slip ring and the brush electrode for making an electrical connection with the slip ring are not necessary, which greatly reduces sparks and breakdowns to improve the reliability. In addition, the annual maintenance cost for maintaining the optimal system performance such as periodical parts replacement and maintenance can be greatly reduced. Furthermore, the rotational moment of the rotating part after each imaging operation is converted into electric energy to be recovered, and the recovered electric energy can be reused for the rotational movement at the next imaging operation. As a result, it may reduce the size of the built-in rechargeable battery in the rotating part, shorten the charging time, or increase the number of times of photographing after charging. Moreover, since the components in the gantry, such as the X-ray source, the X-ray detector, and the rechargeable battery have a cartridge structure, the gantry itself does not need to be disassembled and repaired, and only the defective part is extracted, and a new part is installed instead. As a result, annual maintenance costs and equipment downtime to keep optimal performance of the CT system all the time may be greatly reduced. By replacing the gantry itself, the light source or the detector module according to the diagnostic purposes, it may not be necessary to install all kinds of image diagnostic apparatus like X-ray CT and PET (Positron Emission Tomography), for example, as for the orthopedic surgery, cardiology, and gastroenterology fields. According to at least one example embodiment of the inventive concepts, one hybrid CT system can be applied to various diagnoses in different medical fields. Even in an operating room or inpatient ward in a hospital, doctors can quickly and easily determine the initial diagnosis and treatment plan at the bedside without moving emergency or seriously injured patients who were carried in due to an accident. The CT system can be made smaller and lighter, and the power consumption or the load of repair and maintenance can be reduced. Therefore, the CT system can be moved by a vehicle and enables a quick and accurate initial diagnosis even in a remote place or in the area hit by a disaster, developing countries, other remote areas or depopulated areas by providing the latest and high-level medical services. As a result, the medical disparities due to natural disasters or regional conflicts, for example, can be eliminated.

By changing the gantry, the light source or the sensor cartridges, or adding the gantry for PET or the gantry using the near infrared light source in one CT system, multi-image diagnosis obtained from different light source energies can be realized in a variety of medical fields such as orthopedic surgery, circulatory organ, digestive organ departments, for example. Further, world-wide advanced medical activities will be expanded with the widespread of highly functional medical examination vehicles equipped with inspection equipment like the CT system disclosed in at least one example embodiment.

According to at least one example embodiment, a computed tomographic (CT) system may include a gantry including a rotating part. The rotating part may include a light source, a light source drive control circuit, a rechargeable battery, and a rotating part interface. The gantry may further include, inside or outside the rotating part, a detector, a detector control and signal processing circuit configured to drive the detector and process an output signal from the detector, and an image memory configured to record the output signal of the detector. The rotating part may be configured to rotate around a central axis of a body axis direction. The CT system may further include a gantry table, the gantry mounted on the gantry table, the gantry table including a host interface. The CT system may further include a motor configured to cause the gantry to move in relation to the gantry table in the body axis direction between positions in relation to the gantry table within a gantry moving range. The CT system may further include a control unit configured to process and display image data obtained from the gantry. The rotating part interface may be configured to face the host interface, such that the rotating part interface and the host interface face each other and are configured to be electrically connected with each other, based on the gantry being at a predetermined position in relation to the gantry table within the gantry moving range.

The predetermined position may be an end point of the gantry moving range.

The rotating part interface and the host interface may be configured to face each other in a vertical direction based on the gantry being at the predetermined position.

The rotating part interface and the host interface may be configured to face each other in the body axis direction based on the gantry being at the predetermined position.

The rotating part interface and the host interface may be mechanical interfaces configured to be electrically connected based on being mechanically contacted with each other, based on the gantry being at the predetermined position, or contactless interfaces configured to be electrically connected in a contactless manner based on an interaction of an electromagnetic field therebetween, based on the gantry being at the predetermined position.

The motor may be inside the gantry.

The CT system may further include a drive motor configured to rotate the rotating part in relation to the gantry. The drive motor may be inside the gantry.

The CT system may further include a cradle above an upper portion of the gantry table in a vertical direction, the cradle being at the predetermined position in relation to the gantry table. The cradle may include the host interface.

The light source may be an X-ray light source that includes an electron beam generating unit, the electron beam generating unit being composed of a carbon nanostructure material.

The detector, the light source, the detector control and signal processing circuit, and the image memory may be inside the rotating part, and the detector and the light source may be at opposite sides of the rotating part such that the central axis is sandwiched between the detector and the light source.

The detector may be an electron multiplication sensor, an avalanche effect sensor, or a photon counting sensor.

The control unit and the gantry may have respective wireless interfaces configured to enable, by wireless communication between the control unit and the gantry, transmitting and receiving a control signal to control movement of the gantry in the body axis direction by wireless communication, or causing the gantry to perform an imaging operation.

The CT system may further include a protective cover above the gantry table, the protective cover extending along the body axis direction.

Inside the rotating part, at least one of the light source, the detector, the rechargeable battery, or the image memory may have a cartridge form including electrical contacts, and the rotating part may have a cartridge receiving space into or from which the at least one of the light source, the detector, the rechargeable battery, or the image memory having the cartridge form is configured to be inserted or removed.

The CT system may further include a second gantry on the gantry table.

The detector may include a sensor array of sensors that are arranged over an entire inner circumference of a fixed part surrounding the rotating part inside the gantry.

The rotating part may include an opening configured to allow light emitted from the light source to pass therethrough in the rotating part. The opening and the light source may be at opposite sides of the rotating part such that the central axis is sandwiched therebetween.

The CT system may further include a plurality of induction coils, permanent magnets; and an energy recovery brake circuit configured to convert an electromotive force in the plurality of induction coils, induced by a moment of inertia about the rotating part, into electric energy. The plurality of induction coils may be arranged along an annular part of the rotating part, the permanent magnets may be arranged along a fixed part of the gantry surrounding the rotating part so that N poles and S poles of the permanent magnets are alternately facing the annular part of the rotating part, and the energy recovery brake circuit may be in the rotating part, or the plurality of induction coils may be arranged along a circumference of a fixed part inside the gantry surrounding a circumference of the rotating part, the permanent magnets may be arranged along the circumference of the rotating part so that N poles and S poles of the permanent magnets are alternately facing the circumference of the fixed part, and the energy recovery brake circuit may be in the fixed part.

The rotating part interface may be configured to face the host interface, such that the rotating part interface and the host interface face each other and are configured to be electrically connected with each other, based on the rotating part being rotated to a particular rotational position where the rotating part interface is at a particular position to face the host interface.

According to at least one example embodiment, a method of driving the CT system may include causing the gantry to begin to move after rotational movement of the rotating part around the central axis has started, performing an imaging operation, the imaging operation including X-ray irradiation of the detector by the light source to cause the detector to generate digital data in response to the X-ray irradiation, recording digital data obtained from the detector in the image memory based on the X-ray irradiation, causing a counter electromotive force in the plurality of induction coils to be recovered by the energy recovery brake circuit as electric energy being caused by rotational kinetic energy of the rotating part, such that the rotational movement is decelerated while the energy recovery brake circuit charges a capacitor or the rechargeable battery with the electric energy, causing the gantry to stop at the predetermined position, and causing the digital data recorded in the image memory to be read from the rotating part interface through the host interface.

BRIEF DESCRIPTION OF THE DRAWINGS

The above and other features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 5(a) is a diagram illustrating an X-Y plan view of a CT system, particularly the gantry section as seen from the Z-axis direction, according to at least one example embodiment.

FIG. 5(b) is a diagram illustrating a cross sectional structure of the CT system shown in FIG. 5(a) as seen from the X-axis or Y-axis direction, according to at least one example embodiment.

FIG. 5(c) is a diagram illustrating an enlarged plan view of a portion A indicated by a broken line in FIG. 5(a), according to at least one example embodiment.

FIG. 5(d) is a diagram illustrating a plan view of the opening formed in the rotating part, as viewed from the X-ray generator, where more than two sensor units can be seen through the opening formed in the fixed part, according to at least one example embodiment.

FIG. 7(a) is a diagram illustrating a side view of a CT system as seen from the X-axis direction, according to at least one example embodiment.

FIG. 7(b) is a diagram illustrating a plan view of the CT system shown in FIG. 7(a), as seen from the Z-axis direction.

FIG. 7(c) is a diagram illustrating an enlarged view of a portion B indicated by a broken line in FIG. 7(a).

DETAILED DESCRIPTION OF EXAMPLE EMBODIMENTS

Figure 1A:
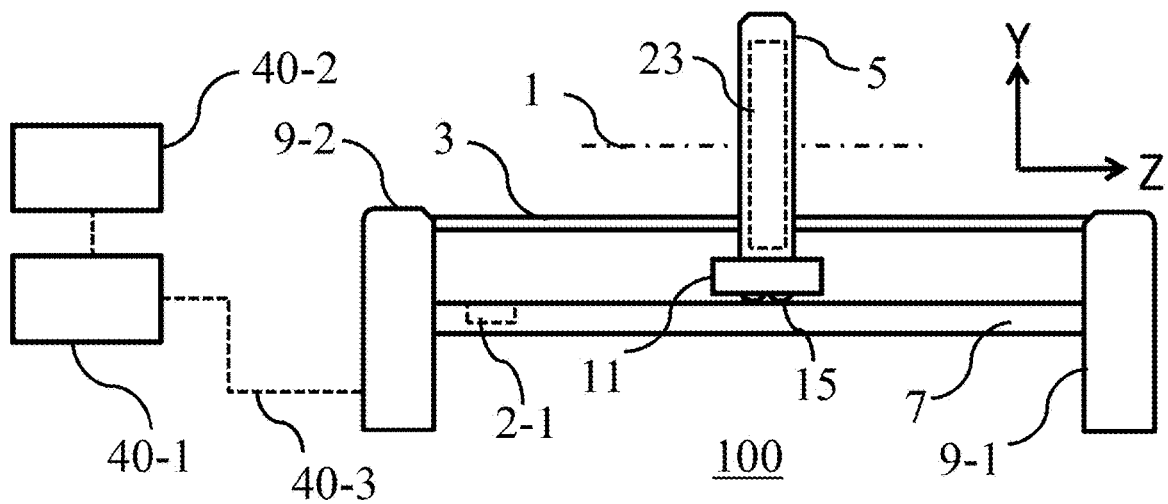
FIG. 1(a) is a diagram illustrating a side view of a CT system with a view direction parallel to the X-axis, according to at least one example embodiment.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, example embodiments of the inventive concepts are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected to", "coupled to", or "on" another element, it may be directly connected to, directly coupled to, or directly on the other element, or intervening elements may be present. In contrast, when an element is referred to as being "directly connected to", "directly coupled to", or "directly on" another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In at least one example embodiment of the inventive concepts, the gantry or the bed movement direction, that is, the body axis direction is defined as the Z-axis, and the plane perpendicular to the Z-axis is defined as the X-Y plane. With reference to the FIGS. 1(a)-1(c), a CT system 100 is described according to at least one example embodiment. The FIG. 1(a) shows a side view of the CT system 100 as seen from the X-axis direction. The CT system 100 has a structure including a gantry table 7, pedestals (9-1 and 9-2) supporting the gantry table 7, and a gantry 5 movable in the Z-axis direction on the gantry table 7, such that the gantry 5 is movable in relation to the gantry table 7 in the Z-axis direction between various positions in relation to the gantry table 7 within a gantry moving range. A rotating part 23 with a rotation center axis 1 (also referred to herein as a central axis of the Z-axis direction) is placed inside the gantry 5. An operation and control part, also referred to herein interchangeably as a control unit 40-1, and a display monitor 40-2 are provided. The control unit 40-1 and the display monitor 40-2 are communicatively coupled to each other as shown in FIG. 1(a), such that the display monitor 40-2 is configured to display images based on signals generated at the control unit 40-1 and transmitted to the display monitor 40-2. The control unit 40-1 is communicatively coupled (also referred to herein as electrically coupled) to at least the gantry table 7 via cable 40-3. A tomographic image reconstructed by an imaging circuit and software (e.g., by at least the control unit 40-1) in response to an imaging operation being performed by some or all of the CT system 100 may be displayed on the display monitor 40-2. A movable gantry carriage 11 has a drive unit (e.g., gantry carriage driving motor 17) configured to move the gantry 5 in the Z-axis direction within the gantry moving range, and wheels 15 are attached to the lower portion of the gantry 5. Further, as described in detail below, the electrical connection means for transferring an electric signal or electric power between the rotating part 23 in the gantry and the gantry table 7, host interface 2-1, is shown on the upper part of the gantry table and the rotating part side (shown in FIG. 1(c), not shown in FIG. 1(a)) in the gantry 5. The bed 3, on which a subject or other examination objects can be placed, is inserted through an inner side of the gantry 5 in the Z-axis directions. The gantry 5 moves in relation to the gantry table 7 in the Z-axis direction between positions in relation to the gantry table 7 within a gantry moving range during the examination, and on the other hand, the subject on the bed 3 stays in one place together with the bed 3. With the configuration described above, a robust and precise control subject movement means is not required, and thus the weight of the CT system 100 itself can be reduced. In addition, as will be described in detail below, the scanning speed in the body axis (Z-axis) direction of the gantry 5 can be increased without increasing physical or mental distress and load of patients.

Figure 1B:
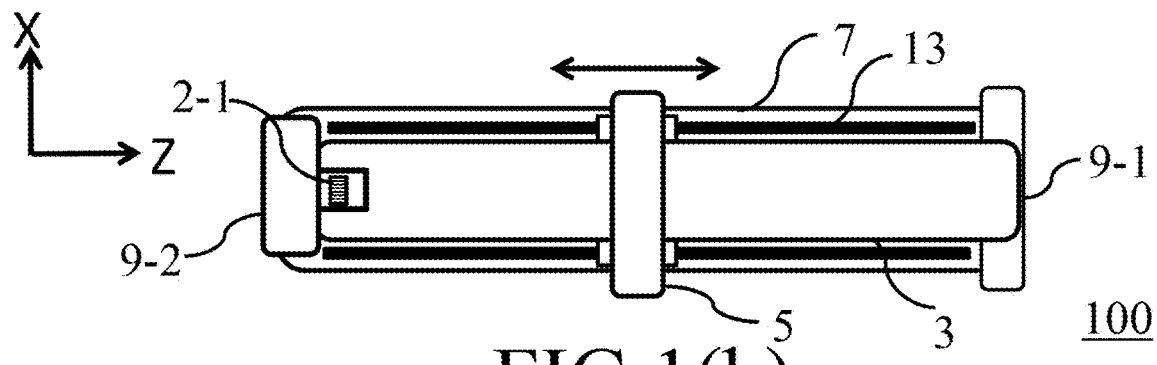
FIG. 1(b) is a diagram illustrating a plan view of the CT system of FIG. 1(a) from a top side of the CT system with a view direction parallel to the Y-axis, according to at least one example embodiment.

FIG. 1(b) shows a plan view of the CT system 100 viewed from the Y-axis direction. Two rails 13, on which the gantry 5 moves along the gantry table 7, are laid on the gantry table 7. Using a conductive material such as metal for the rail 13 and the wheels 15, electric power can be supplied to the gantry carriage driving motor 17 installed inside the movable gantry carriage 11, or control signals can be transmitted to and from the movable gantry carriage 11. As described above, the host interface 2-1 which is an electrical connecting means for exchanging an electric signal or electric power between the rotating part 23 inside the gantry and the gantry table 7. The host interface 2-1 is provided at a predetermined position on the upper part of the gantry table 7 within the range where the gantry 5 can move. For example, the host interface 2-1 may be located at a position that is aligned, in a particular direction (e.g., in the Y-axis direction) with a predetermined position of the positions within the gantry moving range to which the gantry 5 may be moved in the Z-axis direction, such that the host interface 2-1 may be aligned with the rotating part interface 2-2 based at least in part upon the gantry 5 being moved to the predetermined position. The predetermined position, for example as shown in FIGS. 1(a)-1(b), may be an end point of the gantry 5 movable range (also referred to herein as the gantry moving range) in the Z-axis direction. The predetermined position is not limited to the end point of the movable range of the gantry 5 so long as the position will not cause any problems when a subject such as a patient is examined, for example. In this example embodiment, the bed 3 is placed above the pedestal 9-1 and 9-2, and thus can be easily removed. Therefore, instead of the bed 3, a subject holding means having another shape, for example, a movable stretcher type bed may be used. In addition, it is easy to remove the bed 3, and then remove the gantry 5 from the gantry table 7. As a result, it becomes easy to perform the maintenance or replacement of the gantry 5. Further, the light source in the gantry 5 can be easily replaced with another light source having different energy or wavelength showing different imaging characteristics.

Figure 1C:
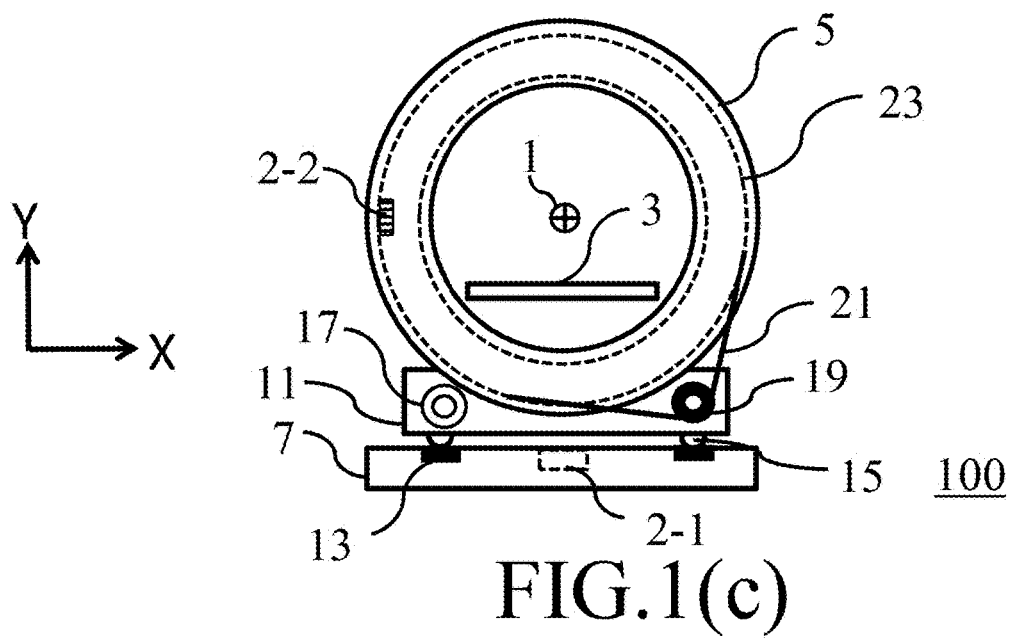
FIG. 1(c) is a diagram illustrating a plan view of the CT system of FIG. 1(a) with a view direction parallel to the Z-axis, according to at least one example embodiment.

FIG. 1(c) shows a plan view of the CT system 100 viewed from the Z-axis direction. Inside the gantry 5, a rotating part 23 that rotates around the rotation center axis 1 is attached using ball bearings (not shown in the figure), for example. Further, a timing belt 21 for rotating the rotating part 23 is attached to a gantry rotating motor 19 inside the movable gantry carriage 11. As will be described below, the energy recovery brake circuit 50 may be incorporated inside the rotating part 23. Further, since the rotating part 23 has the rotating part interface 2-2, it can be electrically connected to the host interface 2-1 at a position facing the host interface 2-1 when the rotating part 23 is stationary. Restated, the rotating part 23 may be configured to rotate around the central axis 1 between various rotational positions, and the rotating part interface 2-2 may be configured to face the host interface 2-1, such that the rotating part interface 2-2 and the host interface 2-1 face each other and are configured to be electrically connected with each other, based on the rotating part 23 being rotated to a particular rotational position where the rotating part interface 2-2 is at a particular position to face the host interface 2-1, in addition to the gantry 5 being moved to the predetermined position as described above. A position sensor (not shown in the figure) using a Hall effect sensor, for example, can be used so that the rotating part 23 stops rotating at a particular rotational position so that the rotating part interface 2-2 stops at the position where the rotating part interface 2-2 face and the host interface 2-1 face are face to face with each other.

It will be understood that, when the rotating part interface 2-2 face and the host interface 2-1 face are face to face with each other, opposing, or proximate faces of the rotating part interface 2-2 and the host interface 2-1 may be understood to be at least partially aligned (e.g., overlapped) in a particular direction (e.g., a direction that is normal to the proximate faces of the rotating part interface 2-2 and the host interface 2-1), such as the Y-axis direction in FIGS. 1(a)-1(c), and the rotating part interface 2-2 and the host interface 2-1 may thus be understood to be face to face with each other. When the rotating part interface 2-2 and the host interface 2-1 are face to face with each other, respective terminals and/or connectors of the rotating part interface 2-2 and the host interface 2-1 may be aligned and configured to mechanically engage with each other. When the rotating part interface 2-2 and the host interface 2-1 are face to face with each other, a distance between the rotating part interface 2-2 and the host interface 2-1 over the positions of the gantry 5 in the gantry moving range, and potentially further over the rotational positions of the rotating part 23, may be minimized. The rotating part interface 2-2 and the host interface 2-1 may be configured to be electrically connected with each other when the rotating part interface 2-2 and the host interface 2-1 are face to face with each other.

Accordingly, it will be understood that the rotating part interface 2-2 may be configured to face the host interface 2-1, such that the rotating part interface 2-2 and the host interface 2-1 face each other, based on the gantry 5 being at a predetermined position in relation to the gantry table 7 within the gantry moving range. In at least one example embodiment, the rotating part interface 2-2 may be configured to face the host interface 2-1, such that the rotating part interface 2-2 and the host interface 2-1 face each other and are configured to be electrically connected with each other, based on the rotating part 23 being rotated to a particular rotational position where the rotating part interface 2-2 is at a particular position to face the host interface 2-1, (e.g., opposing, or proximate, faces of the rotating part interface 2-2 and the host interface 2-1 are at least partially aligned in a direction that is normal to said opposing faces).

Figure 2A:
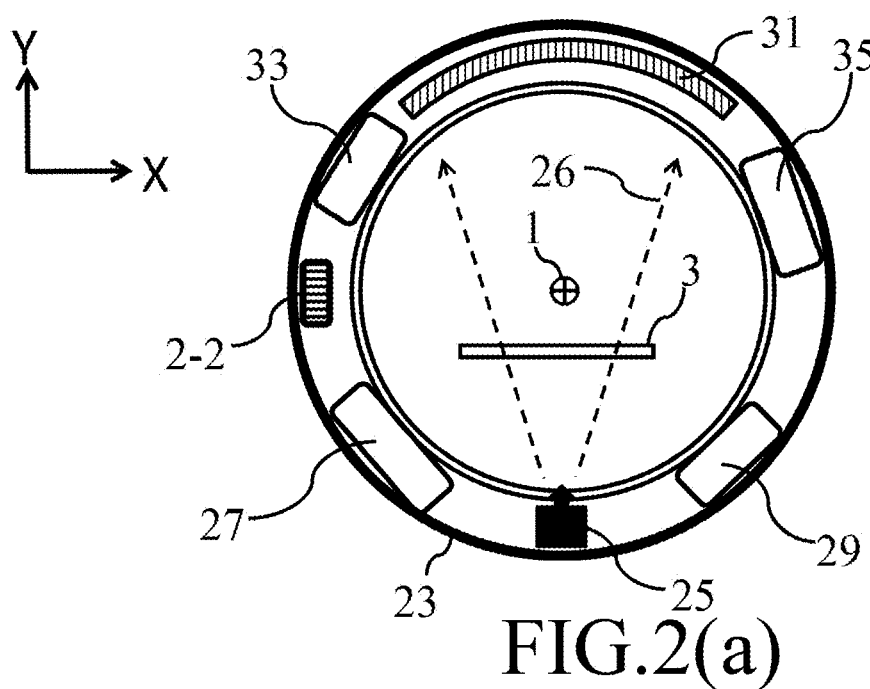
FIG. 2(a) is a diagram illustrating a plan view with a view direction parallel to the Z-axis direction showing the internal structure of the rotating part inside the gantry, according to at least one example embodiment.
Figure 2B:
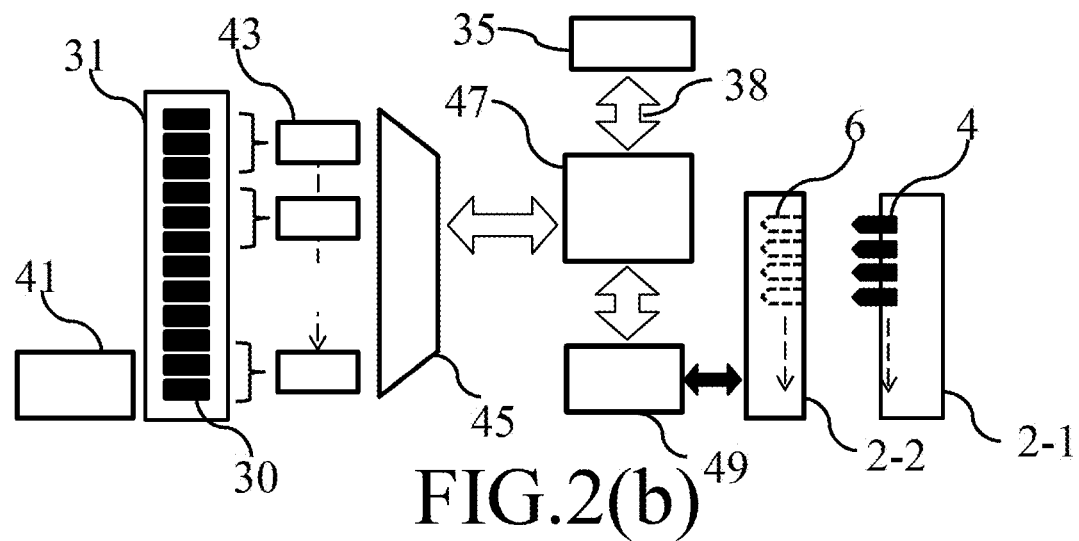
FIG. 2(b) is a diagram illustrating a block diagram of an electric circuit, particularly the sensor array and its peripheral circuit used inside the rotating part of the CT system, according to at least one example embodiment.

As described further below with reference to at least FIG. 2(b), the rotating part interface 2-2 and the host interface 2-1 may be mechanical interfaces configured to be electrically connected based on being mechanically contacted with each other, based at least on the gantry 5 being at the predetermined position. As described further below with reference to at least FIG. 3(b), the rotating part interface 2-2 and the host interface 2-1 may be contactless interfaces configured to be electrically connected in a contactless manner based on an interaction of an electromagnetic field therebetween, based on the gantry 5 being at the predetermined position.

Further, a gantry carriage driving motor 17 for moving the gantry 5 in the Z-axis direction is provided inside the movable gantry carriage 11. The electric power for the driving motor can be supplied from the rails 13 as described above, or a secondary battery, also referred to herein interchangeably as a rechargeable battery, can be built inside the movable gantry carriage 11 instead.

Further, as a moving means for moving the gantry 5 in the Z-axis direction, as will be described later (FIG. 3(a), for example), another configuration of towing from the pedestal (9-1 or 9-2) side may be also used. With these configurations, unlike the conventional case, the rotating means of the rotating part 23 in the gantry can be arranged on the movable gantry carriage 11, for example. As a result, it becomes not necessary to fix the gantry to the CT main body, and the gantry can be moved or removed easily. In this example embodiment, the sensor array 31 is incorporated inside the rotating part 23. As is discussed in detail below, the sensor array 31 can be placed around the entire inner circumference of the gantry 5, which surrounds the rotating part 23 as will be shown in FIGS. 4(a)-4(c), for example.

The control unit 40-1 may include any well-known structure for implementing a CT system control unit, The control unit 40-1, and/or any portions thereof (including, without limitation, any circuits, units, modules, and/or devices described herein according to any example embodiments) may include, may be included in, and/or may be implemented by one or more well-known instances of processing circuitry for implementing a control unit of a CT system, such as hardware including logic circuits; a hardware/software combination such as a processor executing software; or a combination thereof. For example, the processing circuitry more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), and the like. In at least one example embodiment, the processing circuitry may include a non-transitory computer readable storage device, for example a solid state drive (SSD), or a semiconductor memory such as a DRAM or a NAND flash memory, storing a program of instructions, and a processor, for example a CPU, configured to execute the program of instructions to implement the functionality and/or methods performed by some or all of the control unit 40-1.

In at least one example embodiment, the control unit 40-1 may include well-known hardware for implementing a CT system control unit, including, without limitation, a processor, also referred to herein as processing circuitry, a memory, also referred to herein as a non-transitory computer readable storage device, and one or more communication interfaces (e.g., wired and/or wireless communication interfaces, transceivers, etc.) configured to communicatively couple (e.g., electrically couple) the control unit 40-1 to one or more external devices. The aforementioned processor, memory, and communication interface(s) may be communicatively and/or electrically coupled to each other via a communication bus. The memory may store a program of instructions, and the processor may access and execute the program of instructions to implement some or all of the functionality of the control unit 40-1.

The display monitor 40-2 may include any well-known device for implementing a display monitor for a CT system, including a light-emitting diode (LED) display device, organic light-emitting diode (OLED) display device, cathode ray tube (CRT) display device, or the like. As shown in FIG. 1(*a*), the control unit 40-1 may be communicatively coupled to the display monitor 40-2 and may generate and transmit power and/or control signals to the display monitor 40-2 to cause the display monitor 40-2 to display one or more images.

As shown in FIG. 1(*a*), the control unit 40-1 may be communicatively coupled to the gantry table 7 via a cable 40-3 (e.g., a wired connection) which may be communicatively coupled (e.g., electrically coupled) to the host interface 2-1, the rails 13, or any portion of the CT system 100 via conductive elements and/or circuits of the gantry table 7.

As described herein, in some example embodiments, the control unit 40-1 may include one or more wireless communication interfaces, including ad hoc wireless network communication interfaces (e.g., Bluetooth®, 5G, etc.) to establish a wireless communication link between the control unit 40-1 and one or more portions of the CT system (e.g., the rotating part 23) without a wired communication link therebetween.

Figure 2C:
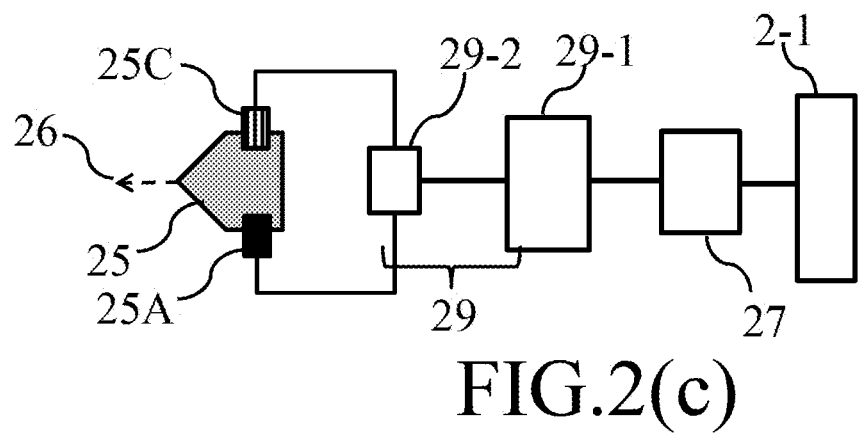
FIG. 2(c) is a diagram illustrating a block diagram of an electric circuit, particularly the X-ray generator and light source driving circuit used inside the rotating part of the CT system, according to at least one example embodiment.

With reference to FIGS. 2(*a*)-2(*c*), the internal structure of the rotating part 23 of the CT system 100, particularly the electric circuit is discussed in detail. FIG. 2(*a*) is a plan view of the rotating part 23 from the Z-axis direction, showing components used inside the rotation part 23. A light source such as an X-ray generator 25, a high voltage control circuit 29, a sensor array 31 (also referred to herein as a detector), a sensor peripheral circuit 33, a sensor driving and control circuit 41, a digital signal processing circuit (not shown in this figure), the image memory 35, the rechargeable battery 27, and the rotating part interface 2-2 are placed inside the rotation part 23. A "rechargeable battery," such as rechargeable battery 27, is also referred to herein interchangeably as a "secondary battery," such as a lithium ion battery. While the light source is described herein as an X-ray generator 25, it will be understood that example embodiments are not limited thereto: the light source may be an X-ray light source (e.g., X-ray generator) or a near infrared (NIR) light source, for example. As is discussed in detail below, the X-ray generator 25, the rechargeable battery 27, and the image memory 35 may have a cartridge type structure, which can be easily inserted or removed individually to or from the rotating part 23. Each cartridge and the rotating part 23 can be electrically connected by metal contacts between these two portions. The rotating part interface 2-2 may be a non-contact interface described below in detail, or a contact interface (also referred to herein as a mechanical interface) using an electrically conductive electrode. The X-ray beam 26 emitted from the X-ray generator 25 is transmitted through a subject (not shown in the figure) on the bed 3 and reaches the sensor array 31 (e.g., implement X-ray irradiation of the sensor array 31, where the sensor array 31 may be configured to sense the incident X-ray beam and generate an output signal (e.g., digital data) based on said X-ray irradiation). A weight balance unit which adjusts the weight balance during the rotating part rotates may be provided. Preferably, the X-ray generator 25 may be an X-ray generator using a carbon nanomaterial such as carbon nanotube (CNT), for example, as a field electron emission source. Using the carbon nano material as the cold cathode material, preheating may not be required, and then the size and power consumption of the X-ray generator 25 can be reduced as compared with the case of conventional X-ray tube, and the high voltage control circuit 29 can be downsized, and a cooling fan can be downsized or even eliminated. In at least one example embodiment, the sensor array 31 is incorporated inside the rotating part 23. Alternatively, as will be described in detail below, the sensor array 31 may be placed around the entire inner fixed portion of the gantry 5 (FIGS. 4(*a*)-4(*c*) and FIGS. 5(*a*)-5(*d*), for example), such that the sensor array 31 may be outside the rotating part 23. In such a case, some of the sensor peripheral circuits, an image memory device, and a host interface, for example, may be located at the fixed part of the gantry 5 and thus may also be outside the rotating part 23.

FIG. 2(*b*) is a circuit block diagram used inside the rotating part 23, particularly showing the sensor array 31 and its sensor peripheral circuit 33 explained in FIG. 2(*a*), which includes a sensor driving and control circuit 41, a signal amplifying and AD converter circuit 43, a signal scanning and control circuit 45, a digital signal processing circuit 47, and a parallel to serial conversion circuit 49, for example. Some of said circuits may be combined in a single circuit configured to perform the functionality of said circuits. For example, the gantry 5 may include a detector control and signal processing circuit that combines some or all of the sensor driving and control circuit 41, the signal amplifying and AD converter circuit 43, the signal scanning and control circuit 45, the digital signal processing circuit 47, and the parallel to serial conversion circuit 49 and may be configured to drive sensor array 31 and process an output signal from the sensor array 31 (e.g., an output signal generated by one or more sensor units 30 of the sensor array 31 in response to X-ray irradiation thereof). The sensor units 30, and thus the sensor array 31, are configured to generate an output signal (e.g., digital data) based on X-ray irradiation thereof (e.g., said sensor units 30 may generate an output signal based on photoelectric conversion of incident light in response to X-ray irradiation of said sensor units 30). As shown in FIG. 2(*a*) and FIG. 2(*b*), the sensor array 31 has a plurality of sensor units 30 arranged in an arc-shaped and placed regularly in the Z-axis direction in order to increase its slice number or width. As for the sensor unit 30, in addition to the conventional TFT type sensor, a small electron multiplication type sensor (like the Micro PMT element manufactured by Hamamatsu Photonics KK), an avalanche effect type (APD) sensor, an amplification type detector, or a photon counting type detector, for example, can be also used. In addition, a CMOS type sensor which integrates an AD conversion circuit, and a signal processing circuit on-chip, for example, can realize high-speed and low-noise signal reading. Since these sensor units 30 have high sensitivity or low noise characteristics, the total amount of X-ray irradiation or exposure dose can be decreased. It also becomes easy to increase the scanning speed in the Z-axis direction by short-time pulse irradiation. Further, as will be discussed in detail below, if it is not necessary to further increase the X-ray irradiation area, the high current flow with high voltage required for the X-ray generator will not be increased. In addition to reducing the weight of the rotating part 23 by thinning it in the Z-axis direction, the stability and durability of the carbon nanomaterial used as a field electron emission source can be improved. As will be discussed in detail below, the sensor unit 30 has an on-chip scintillator layer which converts an incident X-ray into a visible light corresponding to a band gap of a semiconductor material like a silicon (Si) used for the sensor unit 30. Thus, the sensor unit 30 may generate an output signal based on said visible light (e.g., based on photoelectric conversion of said visible light).

The output signal from the sensor array 31 (generated, for example, based on the sensor unit 30 being irradiated with X-rays generated by the X-ray generator 25) is converted into digital data (16 bits, for example), also referred to herein as "image data," by the signal amplifying and AD converter circuit 43 and sent to the digital signal processing circuit 47 via the signal scanning and control circuit 45. In order to directly record the image data sent from the digital signal processing circuit 47, an image memory 35 is built in the rotating part 23. With this configuration, high-speed memory writing becomes possible because parallel recording can be performed directly on the image memory 35 via the bus line 38 without performing parallel to serial conversion. Although a magnetic recording medium can be used as the image memory 35, a semiconductor memory such as a DRAM or a NAND flash memory may be preferable from the viewpoint of recording speed and reliability. On the other hand, unlike the image capturing step, it may not be necessary to read the image data from the image memory 35 in real time manner. The image data can be read out after the image capturing step (also referred to herein as the imaging operation) is completed and after the rotation of the rotating part 23 and the movement of the gantry 5 are stopped. Thus, the image data can be output as a serial data to the rotating part interface 2-2 via the parallel to serial conversion circuit 49. With such a configuration, the number (e.g., quantity) of terminals in the host interface 2-1 can be reduced by this serialization. Regarding the electrical connecting means between the rotating part interface 2-2 and the host interface 2-1, where the rotating part interface 2-2 and the host interface 2-1 are mechanical interfaces, there are a plurality of connectors inside the rotating part interface 2-2 of the rotating part 23, with the shape of a concave structure like a female connection terminal 6. There are the same number of connection terminals 4 with the shape of a convex structure on the host interface 2-1 side, and then the electrical connection between the rotating part interface 2-2 and the host interface 2-1 can be made by inserting the connection terminals 4 into the concave shape connection terminals 6 when said terminals are aligned, for example when the respective longitudinal axes of the connection terminals 4 are aligned with corresponding respective connection terminals 6, also referred to herein as connectors, connector electrodes, or the like. Such alignment and insertion, to enable electrical connection between the rotating part interface 2-2 and the host interface 2-1 may be enabled when the rotating part interface 2-2 and the host interface 2-1 are face to face with each other (e.g., when the gantry 5 is at the predetermined position, when the rotating part 23 is at the particular rotational position, etc.). Unlike the case using the conventional slip ring which is a dynamic mechanical and sliding contact is used, the image data recorded and stored inside the rotating part 23 is moving (e.g., when the imaging operation is being performed) can be readout from the rotating part interface 2-2 to the host interface 2-1 (e.g., further readout to the control unit 40-1 for processing via electrically connected interfaces 2-2, 2-1 and cable 40-3) during the time when the rotating part 23 is stopped. With such a configuration, the slip ring having undesirable side effects can be eliminated, and high-speed rotation of the rotating part 23, like 2 revolutions per second or more, for example, may be easily obtained. A sensor unit 30 as shown in FIGS. 5(*a*)-5(*d*), for example, will be discussed below. Assuming the number (e.g., quantity) of pixels of the sensor unit 30 in the body axis (Z-axis) direction to be 1000, the arrangement pitch of the pixels to be 50 micron meters (μm), and the rotation speed of the rotating part 23 to be 5 revolutions per second, the moving speed of the gantry 5 in the body axis (Z-axis) direction can be estimated about 25 centimeters (cm) per second. As described above, with reducing the weight and increasing the rotating speed of the rotating part 23, the scanning speed in the body axis (Z-axis) direction can be increased. Therefore, the amount of total X-ray exposure to a body being imaged by the CT system may be reduced without increasing the number of slices in the body direction, and image inspection accuracy can be improved by the pixel miniaturization. In addition, this configuration may be also useful for imaging constantly moving organs such as the human heart.

FIG. 2(*c*) shows a block diagram showing the X-ray generator 25 (also referred to herein as a light source) and the high voltage control circuit 29 (also referred to herein as a light source drive control circuit) inside the rotation part 23. The cartridge type X-ray generator 25 comprises an electron beam generation cold cathode 25C using carbon nanomaterials and an anode target 25A. The high voltage control circuit 29 includes a voltage booster circuit 29-1 and a high voltage control circuit 29-2. Preferably, the high voltage control circuit 29 is a transformer-less high-voltage power supply unit of small size, light weight, and low power consumption using a switching power supply and a power semiconductor. As the rechargeable battery 27 having a cartridge structure, like a lithium ion battery, for example, can be used. Then, the DC voltage of the lithium ion battery 27 can be boosted by the high voltage control circuit 29, and a timing controlled high-voltage pulse can be applied to the X-ray generator 25. The lithium ion battery 27 can be charged by the circuit monitoring the remaining amount of charges in the battery and charged by the charger circuit (not shown) via the rotating part interface 2-2 and the host interface 2-1 during the rotating part 23 being stationary.

Circuits as described herein with reference to any example embodiments, and/or any portions thereof (including, without limitation, the high voltage control circuit 29, the sensor peripheral circuit 33, the sensor driving and control circuit 41, the digital signal processing circuit 47, the parallel to serial conversion circuit 49, and/or the high voltage control circuit 29) may include, may be included in, and/or may be implemented by one or more instances of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), and the like. In some example embodiments, the processing circuitry may include a non-transitory computer readable storage device, for example a solid state drive (SSD), storing a program of instructions, and a processor (e.g., a CPU) configured to execute the program of instructions to implement the functionality and/or methods performed by some or all of any of the circuits as described herein.

Figure 3A:
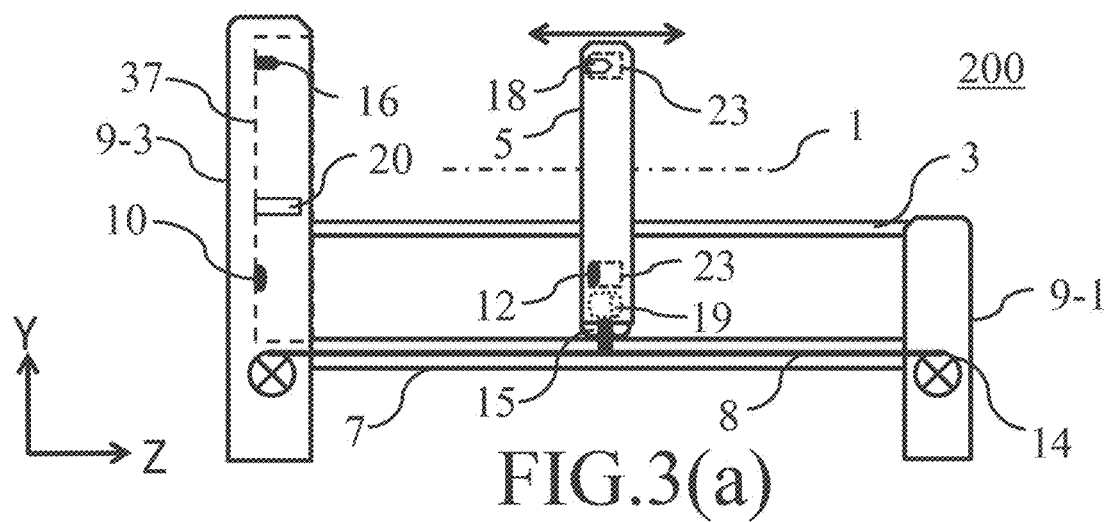
FIG. 3(a) is a diagram illustrating a side view of a CT system as seen from the X-axis direction, according to at least one example embodiment.

FIG. 3(a) shows a side view of the CT system 200 as seen from the X-axis direction according to at least one example embodiment. The parts different from those of above example embodiments described will be discussed in detail below. As shown in FIG. 3(a), the CT system 200 has a portion 9-3 which stands upright in the Y-axis direction from the gantry table 7, which is hereinafter referred to as a cradle 9-3. Inside the rotating part 23, as already described above with reference to FIGS. 2(a)-2(c), the parts having the cartridge structure (not shown in this figure) are used. The cradle 9-3 has a space (indicated by the broken line portion 37) for retracting the gantry 5, the rotating part interface 2-2 of the rotating part 23 inside the gantry 5 is a contactless interface 12, and the host interface 2-1 is a contactless host interface 10. These contactless interfaces are close to each other face to face (e.g., when a distance between the interfaces 10 and 12 is reduced or minimized due to motion of the gantry 5 and/or rotating part 23) such that the interfaces 10 and 12 may be configured to be electrically connected to each other based on an interaction of an electromagnetic field therebetween due to the proximity of the interfaces 10 and 12 to each other, and they can perform non-contact power supply charging the lithium ion battery (e.g., rechargeable battery 27) inside the rotating part 23 and exchanging data or signals between the rotating part 23 and the host side (e.g., control unit 40-1 via the gantry table 7). The arrangement of contactless interfaces of the host interface side 10 and the rotating part side 12 being close to and face each other in the direction of the rotation center axis 1 is illustrated in FIG. 3(a). With this configuration, the non-contact interface 12 can approach the non-contact interface 10 in the direction in which the gantry 5 moves in the Z-axis direction. The gantry 5 has a rotating part 23 which rotates around the rotation center axis 1. The driving method of the rotating part uses the rotation motor 19 and the timing belt 21 (not shown in this figure) as described above. An energy recovery brake circuit (50) may be also incorporated inside the rotating part 23 as discussed in detail below. Further, in the case power is not supplied from the rail 13 for the gantry 5 movement, a rechargeable battery (not shown) may be used in the gantry 5. In this example embodiment, the gantry 5 moves in the body axis (Z-axis) direction by the gantry traction motor 14 provided inside the pedestal 9-1 or the cradle 9-3, and the gantry traction belt 8 along the gantry table 7.

Besides the contactless host interface 10 as described above, a sample holder 20 is provided inside the space 37 in the cradle 9-3. The sample called a standard object or a phantom, for example, is examined in advance whether the sensor (e.g., sensor array 31) or the light source (e.g., X-ray generator 25) used inside the rotating part 23 is functioning properly or not. Further, an inspection probe (not shown in the figure) inspecting or calibrating the rotating part 23 may be provided inside the cradle 9-3. Inside the space 37, a supply port 16 for injecting a cooling gas such as air or nitrogen gas in order to lower the temperature inside the gantry 5 is provided. An opening 18, which is fitted into the supply port 16 is provided in the rotating part 23. A hold mechanism (not shown in the figure) for holding or fixing the gantry 5 in place in relation to the gantry table 7 may be provided inside the space 37. With this configuration, the gantry 5 can be protected from mechanical shock when the CT system 200 is transported or moved. As described above, the cradle 9-3 can provide necessary functions for the stable gantry 5 driving, maintaining safety and system performance.

Figure 3B:
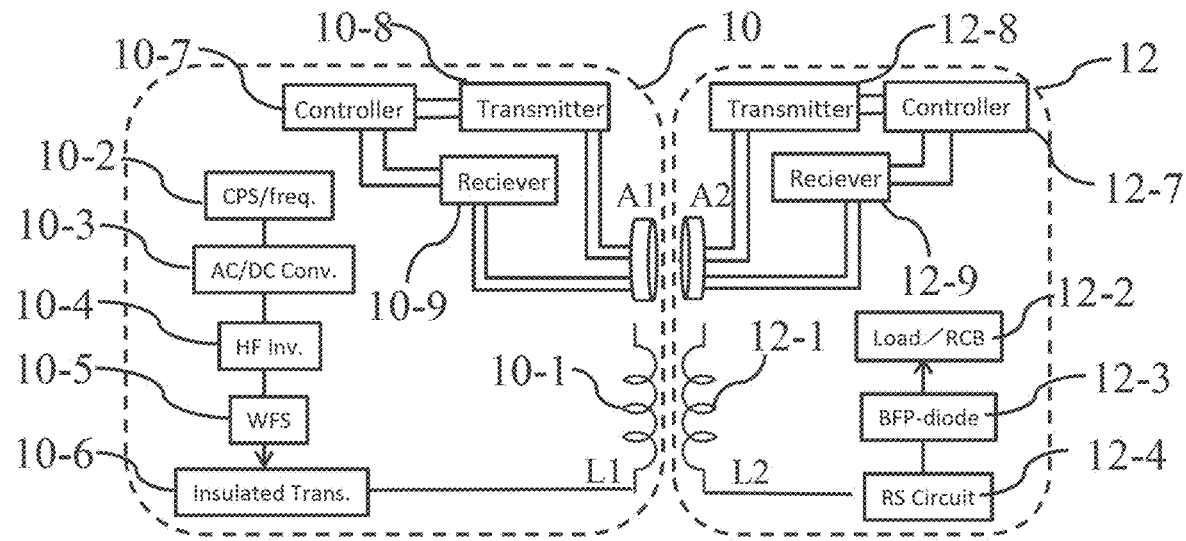
FIG. 3(b) is for explaining a circuit configuration of a wireless power feeding part including the non-contact interface, according to at least one example embodiment.

FIG. 3(b) is a block diagram related to electromagnetic induction type wireless power feeding circuits and wireless communication circuits with respect to the non-contact interface section (10 and 12). As shown in the figure, the circuit configuration on the contactless host interface side (10) includes an AC to DC converter (10-3) that converts a commercial power supply (10-2) (e.g., an external alternating current (AC) power supply network to which the gantry table 7 is communicatively coupled) into a direct current (DC), and a high frequency inverter (10-4) which outputs a high frequency square waveform. A waveform shaping circuit (10-5) converting the square waveform into a sine waveform is connected to the primary winding coil L1 (10-1) via an insulated transformer (10-6) for ensuring safety. On the other hand, the secondary winding coil L2 (12-1) is connected to a load such as a secondary battery (12-2), also referred to herein as a rechargeable battery, via a rectifying and waveform smoothing circuit (12-4) converting the high frequency current to a direct current followed by a reverse current blocking diode (12-3), for example. The contactless interfaces 10 and 12 may be configured to be electrically connected in a contactless manner based on an interaction of an electromagnetic field therebetween, based at least on the gantry 5 being at the predetermined position such that the interfaces 10 and 12 are face to face with each other, such that a distance between the interfaces 10 and 12 is reduced or minimized such that interaction of an electromagnetic field between windings coils L1 and L2 (10-1) and (10-2) is enabled.

As for the transmitting and receiving control signals or image data, a wireless communication system based on near-field magnetic field coupling for example, may be used. As shown in FIG. 3(b), antennas A1 and A2 closely face each other between non-contact interfaces 10 and 12, respectively. As shown in the figure, these antennas A1 and A2 are connected to respective signal receivers (10-9, 12-9), also referred to herein as signal receiver circuits, and respective signal transmitters (10-8, 12-8), also referred to herein as signal transmitter circuits, which are configured to be controlled by respective controller circuits (10-7, 12-7). A spiral coil or a coupling capacitor electrode may be used as the near-field antenna (e.g., antennas A1 and A2), for example. As shown in FIG. 10(c), it may be also preferable to introduce a high-speed and large-capacity communication method such as so-called 5G, for example, enabling a high-speed and a large-capacity CT image data transmission owing to the increased data transfer speed of giga (G) bits per second or more. Further, the wireless power feeding and the wireless communication system may be performed by sharing the same coil or antenna.

Controllers as described herein with reference to any example embodiments, and/or any portions thereof (including, without limitation, controllers 10-7 and 12-7) may include, may be included in, and/or may be implemented by one or more instances of processing circuitry such as hardware including logic circuits; a hardware/software combination such as a processor executing software; or a combination thereof. For example, the processing circuity more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), and the like. In some example embodiments, the processing circuitry may include a non-transitory computer readable storage device, for example a solid state drive (SSD), storing a program of instructions, and a processor (e.g., a CPU) configured to execute the program of instructions to implement the functionality and/or methods performed by some or all of any of the controllers as described herein.

Figure 3C:
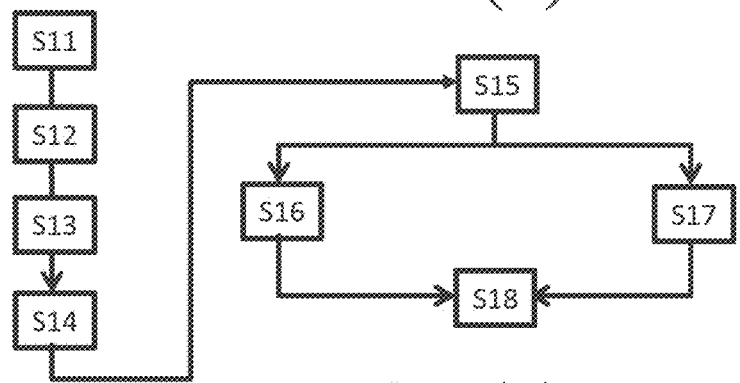
FIG. 3(c) is a flowchart showing a driving method, according to at least one example embodiment.

FIG. 3(c) is a flowchart explaining each step of the driving method for the CT system according to at least one example embodiment. As shown in the figure, after the movement of the gantry 5 and the start of rotation of the rotating part 23 (driving step S11), imaging by X-ray irradiation is started, such that the X-ray generator emits X-rays and the sensor array 31 is subjected to X-ray irradiation by at least some of said X-rays, such that one or more sensor units 30 of the sensor array 31 generate one or more output signals, provided (e.g., via processing of the output signals by one or more circuits) as image data or digital data, in response to said X-ray irradiation (S12). The digital data obtained from the sensor array 31 is recorded in the image memory 35 in real time (S13). As shown in FIG. 2(b), the digital data can be recorded in the image memory 35 as the parallel data without parallel to serial conversion. After the image capturing is completed (S14), the gantry 5 is stopped at a predetermined position in relation to the gantry table 7 such that the rotating part interface 2-2 via the host interface 2-1 are face to face with each other and configured to be electrically connected with each other (e.g., via mechanical engagement of respective connectors when the rotating part interface 2-2 via the host interface 2-1 are mechanical interfaces, or interaction of electromagnetic field therebetween when the rotating part interface 2-2 via the host interface 2-1 are contactless interfaces) (S15), and the data recorded in the image memory 35 is read from the rotating part interface 2-2 via the host interface 2-1 (S16). The data read from the rotating part interface 2-2 via the host interface 2-1 may be communicated to the control unit 40-1 (e.g., via cable 40-3). The control unit 40-1 may perform an image reconstructing process on said data. After the image reconstructing process is performed at the control unit 40-1, the control unit 40-1 may be configured to cause an image based on said reconstructing process to be displayed on the display monitor 40-2, followed by the CT system entering a standby state (S18). The lithium ion battery 27 may be charged (S17) at the same time as the driving step (S16) or during the standby period (S18), and then the driving sequences is completed.

Figure 4A:
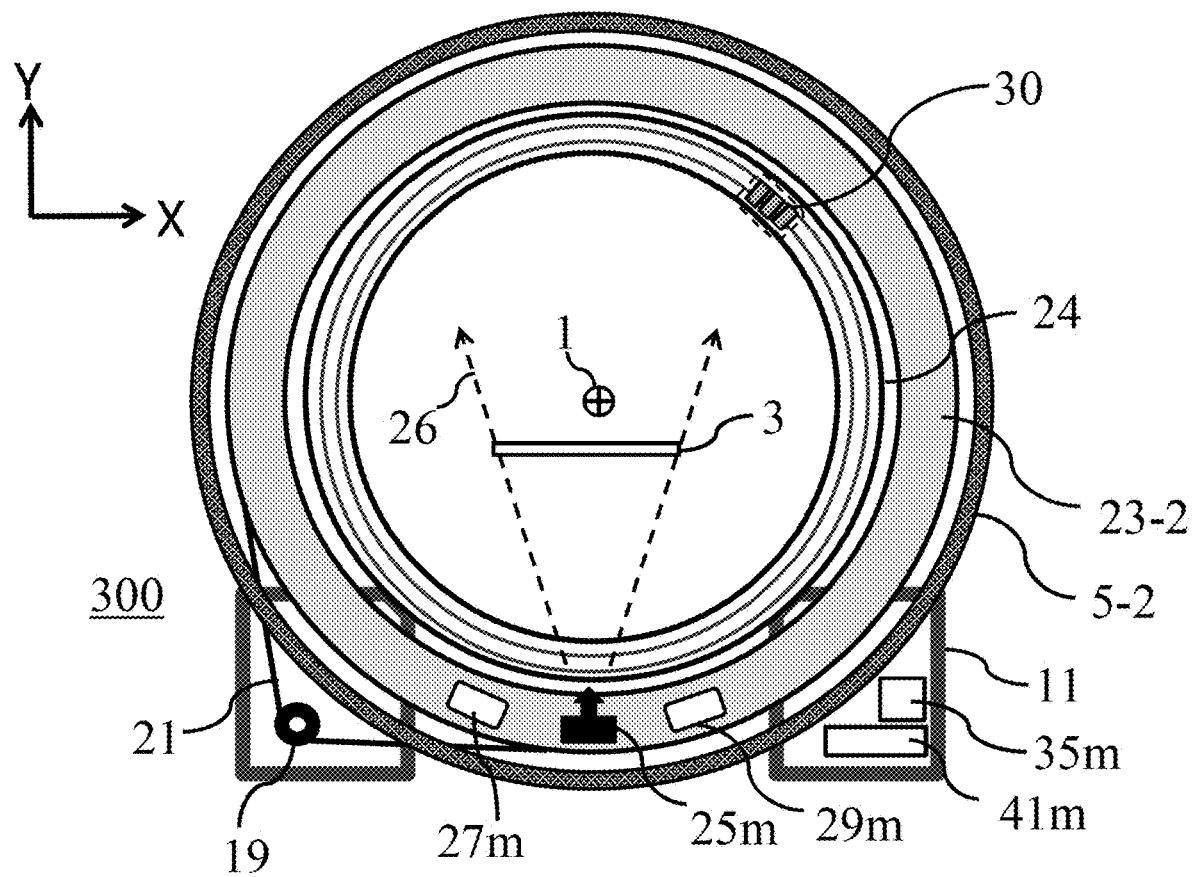
FIG. 4(a) is a diagram illustrating a plan view of the gantry part of a CT system as seen from the Z-axis direction, according to at least one example embodiment.
Figure 4B:
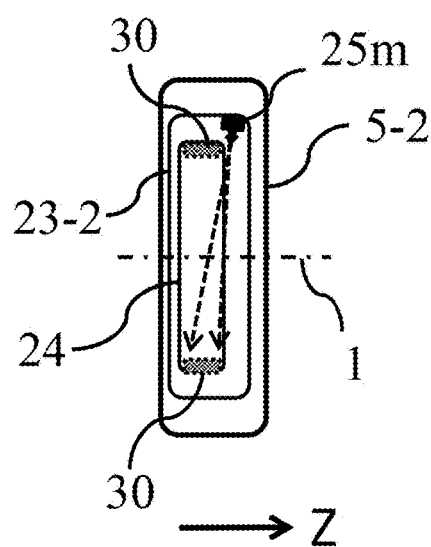
FIG. 4(b) is a diagram illustrating a cross-sectional view seen from the X-axis or Y-axis direction showing the structure of the gantry 5-2 of the CT system shown in FIG. 4(a), according to at least one example embodiment.

FIG. 4(a) is a plan view of the CT system 300, particularly showing the inside structure of the gantry 5-2, as viewed from the Z-axis direction according to at least one example embodiment. FIG. 4(b) is a cross sectional view of the gantry 5-2 used in the CT system 300 with a view direction of the X-axis or Y-axis. As shown in FIG. 4(a), in at least one example embodiment, an X-ray generator 25m, a rechargeable battery 27m, a high voltage control circuit 29m, an energy recovery brake circuit 50 which will be discussed below for example, are placed inside the rotating part 23-2. On the other hand, many sensor units 30 mounted on the entire circumference are placed inside the annular fixed part 24 having the same rotation center as that of the rotating part 23-2. In this example embodiment, the fixed part 24 is attached to the inner peripheral portion of the gantry 5-2 and is located inside the rotating part 23-2 as shown in the X-Y plan view. The gantry rotation motor 19 and the timing belt 21 which rotates the rotating part 23-2 are also described. This setup may be like so-called Nutate-Rotate type CT system. As shown in FIG. 4(b), the X-rays (broken line arrow) emitted from the X-ray generator 25m may be blocked by the fixed part 24, and therefore fixed part 24 is shifted in the Z-axis direction with respect to the mounting position of the sensor unit 30. The X-ray generator 25m, the rechargeable battery 27m, the high voltage control circuit 29m, the image memory 35m, and the sensor driving and control circuit 41m are cartridge type structure, which can be easily attached or detached, as will be described in detail below. With this configuration, the system operation rate is improved, available imaging time is extended, and the system maintenance load is reduced.

Figure 4C:
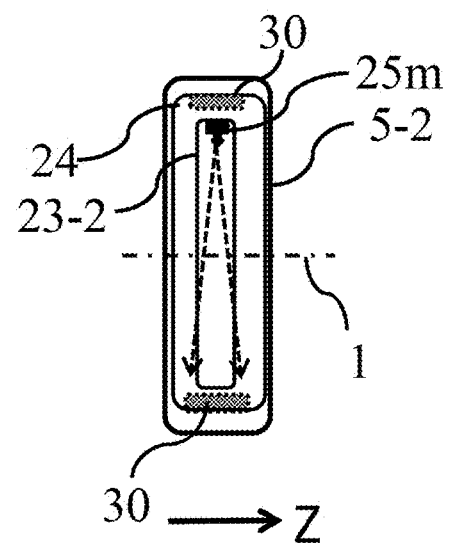
FIG. 4(c) is a diagram illustrating a cross-sectional view seen from the X-axis or Y-axis direction showing the structure of the gantry 5-2 of another variation of the CT system shown in FIG. 4(a), according to at least one example embodiment.

FIG. 4(c) is a cross-sectional view of the internal structure of the CT system according to a variation of the above example embodiment shown in FIG. 4(b), particularly shows the internal structure of the gantry 5-2. The fixed part 24 and the rotating part 23-2 are incorporated inside the gantry 5-2. The difference from the structure shown in FIG. 4(b) is that the diameter of the rotating part 23-2 containing the X-ray generator 25m is smaller than the diameter of the inner peripheral portion of the fixed part 24. The X-rays emitted from X-ray generator 25m can reach the sensor units 30 without being blocked by the fixed part 24. This setup may be like so-called Stationary Rotate type CT system. However, in the case of the conventional structure using a slip ring and electrode brush, their contact surface may heat up causing seizure, and the sensor unit 30 may make an erroneous photoelectric conversion of incident X-rays due to a light emission phenomenon caused by an electric spark when a high voltage or large current flow is applied from the brush electrode to the slip ring sliding with a high speed.

This configuration may cause non-uniform X-ray irradiation of the sensor units 30 because the rotating part 23-2 is located opposed to the X-ray generator 25m in between the central axis of the rotation center and on the optical path of the X-rays emitted from the X-ray generator 25m. A structure that solves this problem will be described below with reference to FIGS. 5(a)-5(d). FIG. 5(a) shows a plan view illustrating the structure of the CT system 400 according to at least one example embodiment, particularly inside the gantry part, as viewed from the Z-axis direction. As described above, the fixed part 24 is combined to surround the outer circumference of the rotating part 23-2. Sensor units 30 (not shown in this figure) are arranged on the entire inner circumference of the fixed part 24. The rotating part 23-2 has an X-ray generator 25m, a light source drive circuit and a secondary battery which is also referred to herein interchangeably as a rechargeable battery (not shown in this figure), for example. An opening 28 marked by a broken line A is formed at the rotating part 23-2, and defined by the rotating part 23-2 so that the X-rays emitted from the X-ray generator 25m can transmit or pass therethrough. With this configuration, intensity of X-ray beam 26 and its traveling direction may not be affected. The opening 28 does not necessarily have to be an empty space where all the members are removed (air only), and a protective cover made of resin having a high X-ray transmittance, for example, may exist. FIG. 5(b) is a cross-sectional view of the structure inside the gantry when the opening 28 is viewed from the X-axis or Y-axis direction. The sensor unit 30 is arranged along the inner circumference of the fixed part 24, and the X-ray beam passing through the opening 28 reaches the sensor unit 30. A fiber optic plate which selectively shields or collimates X-rays, and an X-ray scintillator, for example, may be stacked on the sensor unit 30.

FIG. 5(c) is an enlarged plan view seen from the Z-axis direction showing the structure of the portion indicated by the broken line portion A in FIG. 5(*a*). The sensor units 30 are closely arranged along the annular portion of the fixed part 24 so that the longitudinal direction of the sensor units 30 are parallel to the Z-axis. That is, as shown in FIG. 5(*d*), the same portion will be described with reference to a plan view of the opening 28 being observed from the side of X-ray generator 25*m*. The pixel arrays of the plurality of sensor units 30 attached to the fixed part 24 are directly exposed to the X-ray generator 25*m* through the opening 28 formed in the rotating part 23-2 without shielding the X-ray irradiation.

Figure 6A:
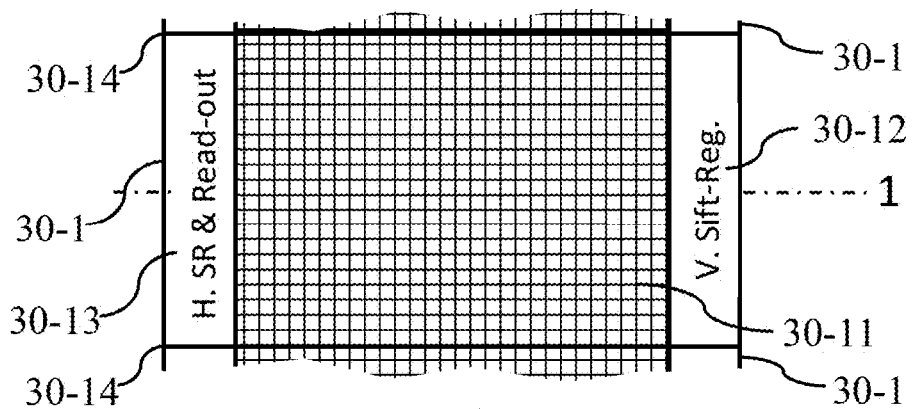
FIG. 6(a) is a diagram illustrating a plan view of a CMOS solid-state image sensor unit suitable for the sensor unit used in a CT system, according to at least one example embodiment.
Figure 6B:
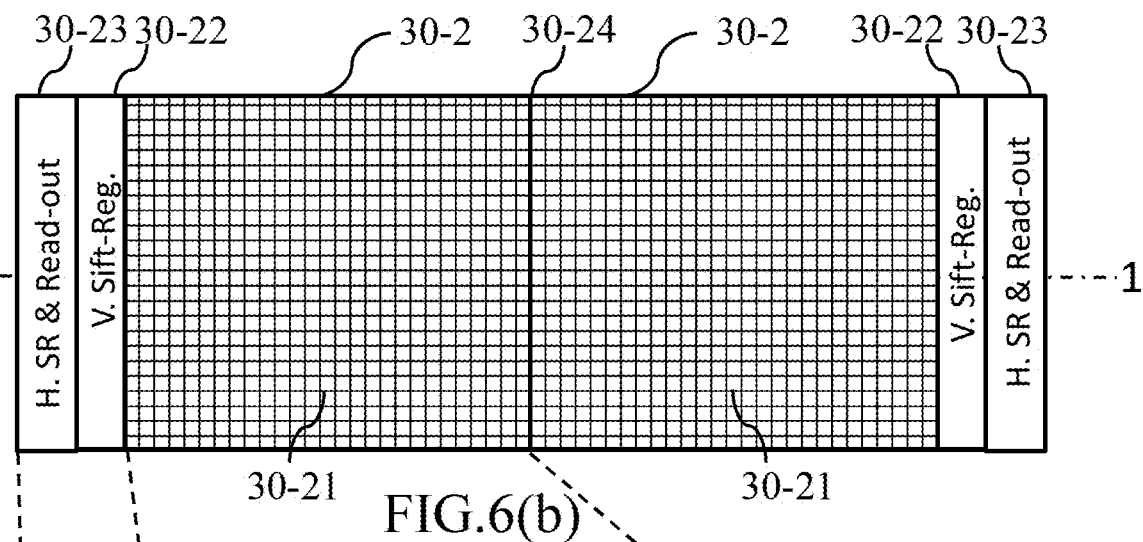
FIG. 6(b) is another sensor unit also suitable for the sensor unit used in the CT system, where the CMOS solid-state image sensors are arranged in close contact with each other as to face each light receiving region closely, according to at least one example embodiment.
Figure 6C:
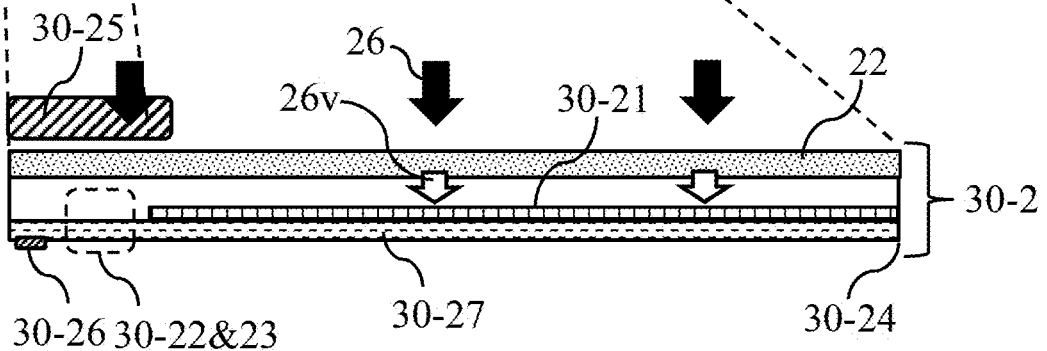
FIG. 6(c) is a diagram illustrating an enlarged cross-sectional view showing the structure of the CMOS solid-state image sensor in FIG. 6(b), according to at least one example embodiment.

With reference to FIGS. 6(*a*)-6(*c*), structure, arrangement and combination of sensor unit 30 which may be suitable for the CT system 300 or 400 will be described below. In FIG. 6(*a*), a plurality of sensor units 30-1 are closely arranged along the inner circumference of the fixed part 24 as to surround the rotation center axis 1. The plurality of sensor units 30-1 are contact with in between the boundary line 30-14, and preferably, the arrangement pitch of the pixels 30-11 in between the boundary line is equal to the arrangement pitch of the pixels 30-11 being not contact with the boundary line 30-14 in the same direction. The structure disclosed in the Japanese Patent No. 5027339, herein incorporated by reference in its entirety, for example may be adopted in such a case. Further, as shown in the figure, the vertical scanning circuit (30-12), and the horizontal scanning and the signal readout circuits (30-13) are placed along the two sides opposite to each other in order not to change the arrangement pitch of each pixel 30-11 described above. Preferably, the sensor unit 30-1 has a larger chip size, and then so-called medium format size (44 mm×33 mm), full format size (36 mm×24 mm) and APS format size (23 mm×15 mm) sensor units which are widely used in digital cameras, for example, can be used based on or optimizing their structure and manufacturing method of CMOS type sensor unit.

FIG. 6(*b*) discloses a configuration where a plurality of sensor units 30-2 are closely arranged along the inner circumference of the fixed part 24 as to surround the rotation center axis 1 and further arranged in the direction of the rotation center axis 1 in order to increase the total number of pixels in the direction of body axis (Z-axis). With such a configuration, the slice width can be enlarged twofold. In at least one example embodiment, the boundary line 30-24 between the left sensor unit 30-2 and the right sensor unit 30-2 in the figure should be considered, because the arrangement pitch of the pixels 30-21 in between the boundary line 30-24 should be equal to the arrangement pitch of the other pixels 30-21 not facing the boundary line 30-24 in the same direction. As already explained above, the structure disclosed in Japanese Patent No. 5027339, herein incorporated by reference in its entirety, may be adopted in such a case. As shown in the figure, the vertical scanning circuit (30-22), and the horizontal scanning and the signal readout circuits (30-23) are placed along the one side of the sensor unit 30-2 in order not to change the arrangement pitch of each pixel 30-21 along the other three sides of the sensor unit 30-2. Three or more sensor units 30 must be arranged in the body axis (Z-axis) direction in order to expand the slice width further. In such a case, the horizontal and vertical scanning circuits and the signal readout circuit (30-22, 30-23) may change the arrangement pitch of the pixels 30-21. An example solution to solve this problem is disclosed in Japanese Patent No. 5424371, herein incorporated by reference in its entirety.

FIG. 6(*c*) is a cross sectional view of the sensor unit 30-2 as shown in FIG. 6(*b*). The sensor unit 30-2 is a backside illuminated CMOS solid-state image sensor having a scintillator layer 22 laminated on the backside. The silicon substrate used in this CMOS solid-state image sensor may be about 5 to 10 micron meter (μm) in thickness because the incident X-ray 26 is converted into a visible light 26*v* in the scintillator layer and the visible light 26*v* is read out as an electric signal by each pixel 30-21. A wiring layer 30-27, horizontal and vertical scanning circuits, signal readout circuits (30-22, 30-23), and connection terminals 30-26 are provided on the front side of the sensor unit 30-2. On the back side, a shield member 30-25, which can reduce the X-ray intensity of incident X-rays and protect the integrated circuit from X-ray damage, is laminated on the horizontal scanning, vertical scanning and the signal readout circuits (30-22, 30-23, respectively).

FIG. 7(*a*) shows a side view of the CT system 500 as viewed from the X-axis direction according to at least one example embodiment. The CT system 500 comprises a bed 3-1, a bed supporting member 3-2 for moving the bed 3-1 and an annular gantry 5. As described above, the gantry 5 has the rotatable rotating part 23 inside, and the rotation center axis 1 is parallel to the Z-axis, or the body axis direction. A fixed part 24 is placed around the rotating part 23 using a ball bearing (not shown in the figure), for example. A portion B surrounded by a broken line with respect to the rotating part 23 and the fixed part 24 will be discussed in detail below. An operation or control unit 40-1 and a display (monitor) unit (display monitor 40-2) (shown in FIG. 1(*a*)) are provided, and a reconstructed tomographic image generated by an image processing circuit and software (which may be implemented by the control unit 40-1 in any of the example embodiments) based on image data provided based on output signals generated by the sensor array 31 in response to X-ray irradiation may be displayed on the display monitor 40-2. The structures of the rotating part 23 and the fixed part 24 of the CT system 500 may be the same as those of the CT system 300 (in FIGS. 4(*a*)-4(*c*)) or the CT system 400 (in FIGS. 5(*a*)-5(*d*)) as explained above.

FIG. 7(*b*) is a plan view of the CT system 500 seen from the Z-axis direction. Inside the annular portion of the gantry 5, a rotating part 23 that rotates around the rotation center axis 1 is installed using ball bearings. A timing belt 21 for rotating the rotating part 23 and a rotating part drive motor (rotating motor 19) are installed. As will be described below, a direct drive (DD) motor configuration may be used such that the rotating part 23 acts as a rotor and the inner circumference of the gantry 5 surrounding the rotating part 23 acts as a stator. FIG. 7(*c*) shows an enlarged view of the portion B in FIG. 7(*a*), and the rotating part interface 6-1 made of a metal electrode is formed on the side surface of the rotating part 23. The rotating part interface 6-1 is located at a position facing the host interface of the convex type connection terminals 4 (also referred to herein as connectors, connector electrodes, or the like), and then the rotating part interface 6-1 can be electrically connected by contacting each other when the rotating part 23 is stationary. Preferably, a position sensor (not shown in the figure) using a Hall effect position sensor, for example may be used so that the convex connection terminal 4 and the rotating part interface 6-1 are stopped at a position facing each other, such that the rotating part interface 6-1 and the convex connection terminal 4 of the host interface 2-1 are face to face with each other as described herein. Alternatively, if the rotating part interface 6-1 is formed in a ring shape over the entire circumference of the annular side surface of the rotating part 23, the rotating part interface 6-1 and the convex type connection terminals 4 may be electrically connected regardless of the stationary position of the rotating part 23.

Figure 8A:
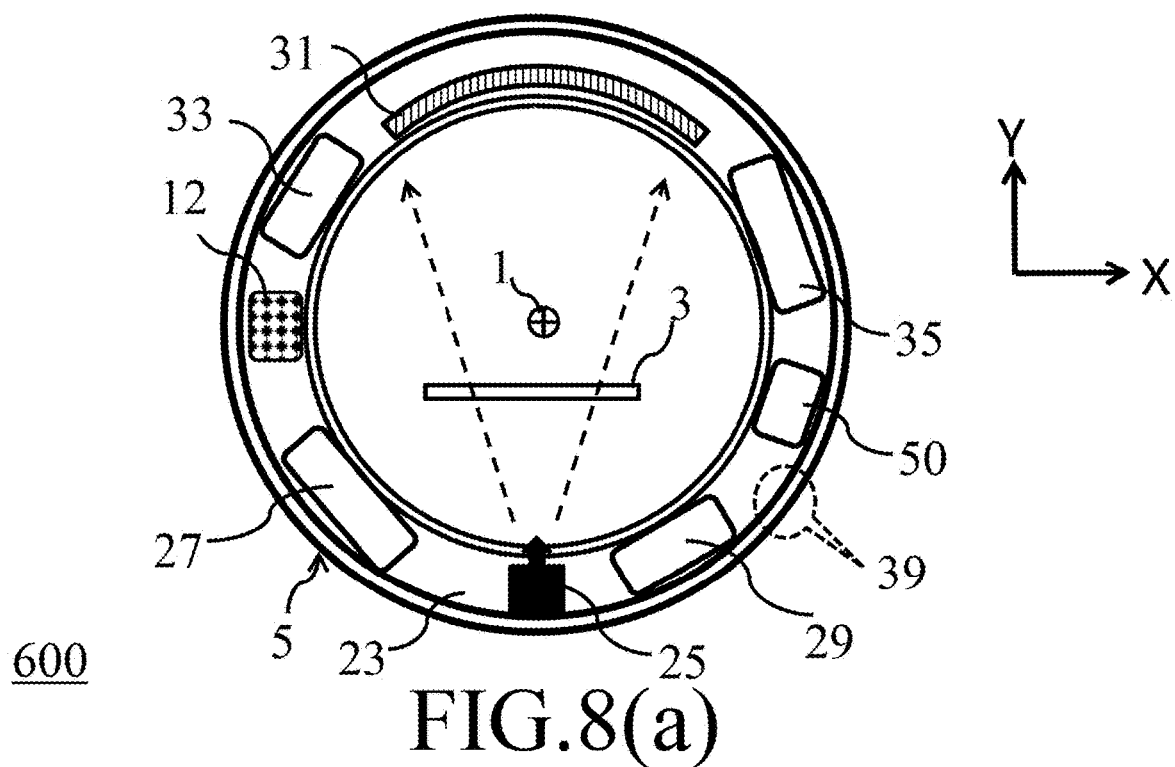
FIG. 8(a) is a diagram illustrating a plan view of a rotating part of the CT system showing inside the gantry as seen from the Z-axis direction at least one example embodiment.
Figure 8B:
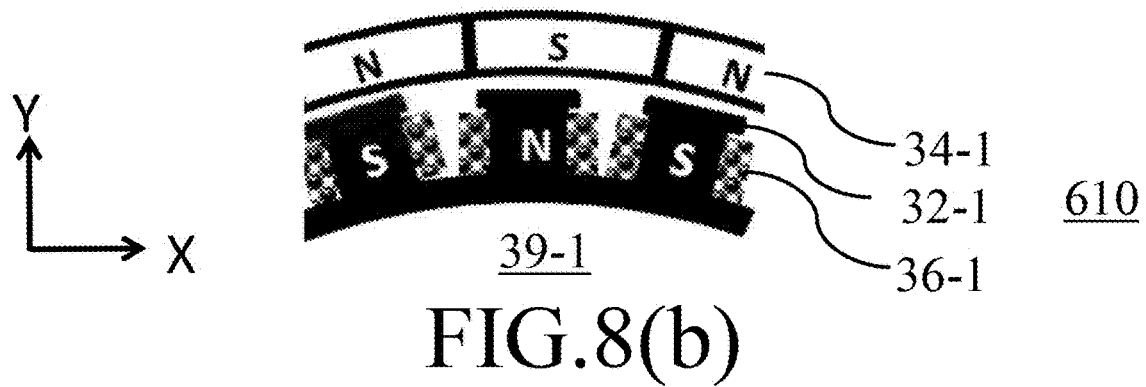
FIG. 8(b) and FIG. 8(c) are diagrams showing partially enlarged views showing the electromagnetic coupling configurations at the portion indicated by the broken line in FIG. 8(a), where the outer circumference of the rotating part is surrounded by the inner circumference of the gantry.
Figure 8C:
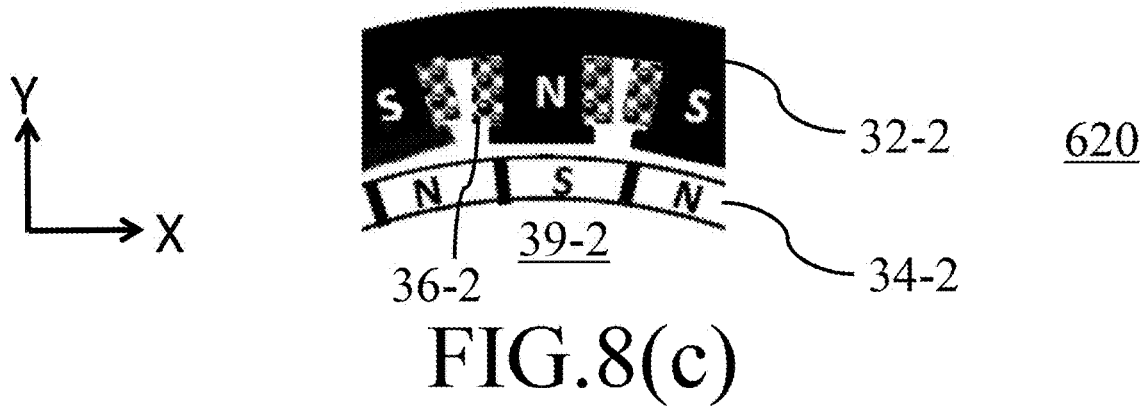

According to at least one example embodiment, the rotating part of the CT system 600, particularly inside the gantry 5 will be described with reference to FIGS. 8(*a*)-8(*c*). FIG. 8(*a*) shows a plan view of the rotating part 23 inside the gantry 5 as seen from the Z-axis direction, and FIGS. 8(*b*) and 8(*c*) show the enlarged structure of the broken line portion 39 in FIG. 8(*a*). As explained above, the rotation part 23 has the X-ray generator 25, the rechargeable battery 27, the high voltage control circuit 29, the sensor array 31, the sensor peripheral circuit 33 including the signal amplification, AD conversion circuit, the signal scanning and control circuit, for example. The sensor driving and control circuit 41, a non-contact interface 12, and a digital signal processing circuit (not shown in the figure), a parallel to serial conversion circuit (not shown in the figure) are also incorporated inside the rotation part 23. As will be described below, the energy recovery brake circuit 50 is placed in the fixed part or the rotating part 23 inside the gantry. The electromagnetic induction coil 36-1, which may in some example embodiments refer to a plurality of induction coils is provided around either the rotating part 23 or the fixed part. The energy recovery brake circuit 50 utilizes the electromotive force induced in the electromagnetic induction coil, to convert an electromotive force in the electromagnetic induction coil 36-1, induced by a moment of inertia about the rotating part 23, into electric energy.

In the structure (39-1) of FIG. 8(*b*), for example, the N pole and the S pole of the permanent magnet (34-1) are alternately arranged along the ring-shaped side of the fixed part so that N poles and S poles of the permanent magnets are alternately facing the annular part of the rotating part. On the side of the rotating part, the induction coil(s) (36-1) is/are wound around the iron core(s) (32-1). Therefore, the energy recovery braking circuit 50 may be provided inside the rotating part 23. On the other hand, in the structure (39-2) of FIG. 8(*c*), for example, the N pole and the S pole of the permanent magnet (34-2) are alternately arranged along the ring-shaped side of the rotating part so that N poles and S poles of the permanent magnets are alternately facing the circumference of the fixed part. On the side of the fixed part, the induction coil(s) (36-2) is/are wound around the iron core(s) (32-2). Therefore, the energy recovery brake circuit 50 may be provided inside the fixed part. This structure may be like that of so-called a direct drive (DD) motor, which is not necessary to rotate the rotating part using an external motor and a timing belt. The structure shown in FIG. 8(*b*) may be preferable if electric energy is stored in the rechargeable battery 27 inside the rotating part 23 or an electric double layer capacitor as described below. In the structure of FIG. 8(*b*), an electromotive force is generated in the induction coil (36-1) even when the rotating part 23 is forcibly rotated by an external motor via a timing belt, as described below, and then it is also possible to charge the rechargeable battery 27. Even after providing the forcible rotation described above, the rotational energy generated in the induction coil (36-1) is recovered to the rechargeable battery or an electric double layer capacitor until the rotation stops as discussed in detail below.

Preferably, a neodymium magnet, for example, may be used as the permanent magnet. As will be described below, the rotational movement of the rotating part inside the gantry is unnecessary after the imaging operation is completed. However, it may be possible to convert the moment of inertia of the rotating part into an electric energy without stopping the rotary motion mechanically, and then energy saving effect can be obtained. The energy recovery brake circuit 50 has such a role in this example embodiment. Rotation (imaging mode) and stop (standby mode) motions are frequently repeated, so that the above mentioned rotation energy recovery effect of the rotating part is remarkable, particularly, in the case of high-speed scanning with increasing the number of rotations of the rotating part.

The energy recovery brake circuit 50 is described below with reference to FIG. 9(*a*). In the CT system according to at least one example embodiment of the inventive concepts, the imaging operation starts after the rotation of the rotating part 23 starts. The imaging operation may include the X-ray generator generating X-rays to irradiate the sensor array 30, such that the sensor array 30 generates one or more output signals in in response to X-ray irradiation thereof by the X-ray generator 25, where said output signals may be processed to provide image data, also referred to herein as digital data. The rotation of the rotating part 23 decelerates, and then the rotational motion stops after completing the imaging sequence. As described above, rotation start and stop motions are repeated within a short time and imaging operations. Effective reuse of the rotational kinetic energy of the rotating part 23 may reduce the power consumption of the rechargeable battery 27 and save energy. The energy recovery brake circuit 50 provided inside the rotating part 23 may include a bidirectional DC-DC converter 42 connected to the rechargeable battery 27, and a DC-AC converter 46 connected to the other end of the bidirectional DC-DC converter 42. The other end of the DC-AC converter 46 is connected to the induction coil 36. The induction coil 36 is connected to a capacitor, preferably an electric double layer capacitor 44, via an AC-DC converter 48. Further, the electric double layer capacitor 44 is connected to the bidirectional DC-DC converter 42. The rotary kinetic energy of the rotating part 23 can be converted into counter electromotive force generated in the induction coil 36, which can charge the electric double layer capacitor 44. Also, the rechargeable battery 27 can be charged via the bidirectional DC-DC converter 42. In general, the energy recovery efficiency using a capacitor may be about 90% or more, which may be higher than that of the case using a rechargeable battery of around 60% efficiency. Particularly, with this configuration, it may be useful for the CT system in which the rotating part 23 is decelerated (energy recovery) and is immediately rotated (discharged) repeatedly. With respect to the bidirectional DC-DC converter 42, a circuit system in which a step-down chopper circuit and a step-up chopper circuit are combined, or a PWM (Pulse Width Modulation) system using a DSP (Digital Signal Processor) and an AD converter may be used.

Figure 9A:
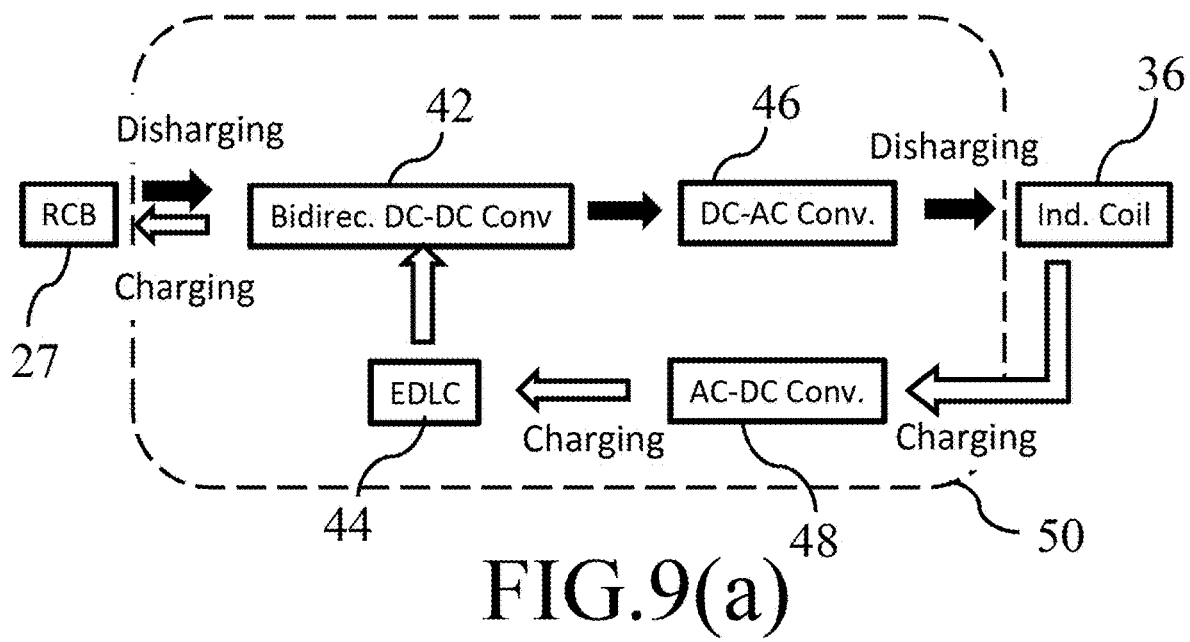
FIG. 9(a) is a diagram illustrating a circuit block used inside the rotating part of the CT system, particularly showing the energy recovery brake circuit at least one example embodiment.
Figure 9B:
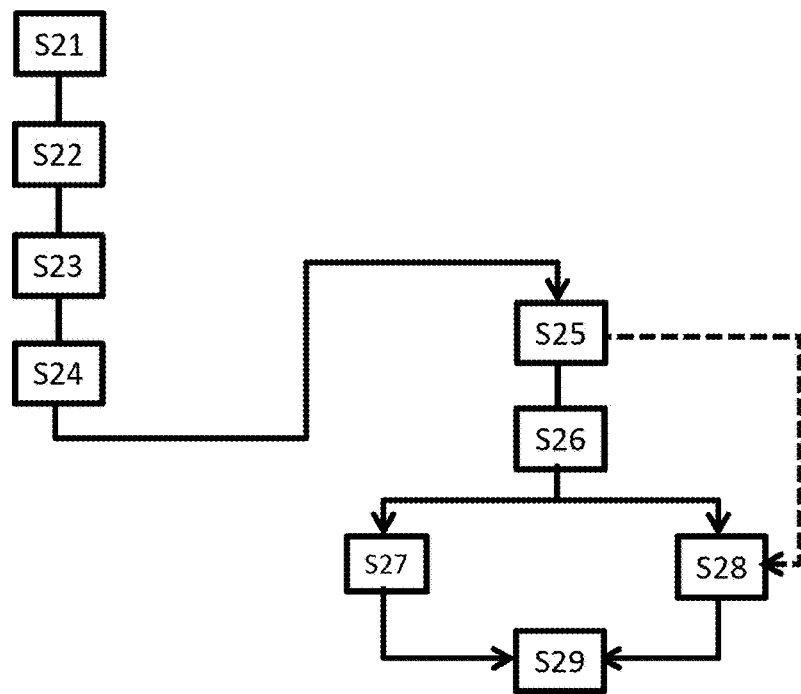
FIG. 9(b) is a flowchart for explaining a driving method of the CT system using the energy recovery brake circuit.

FIG. 9(*b*) is a flowchart describing the driving method when the energy recovery brake circuit is used like the example embodiment shown in FIGS. 8(*a*) and 8(*b*), for example. As shown in the figure, after the rotation of the rotating part 23 is started, then the bed or the gantry begins to move (driving step S21). In the next step, imaging by X-ray irradiation (e.g., the imaging operation) proceeds (S22). The imaging operation may include the X-ray generator generating X-rays to irradiate the sensor array 30, such that the sensor array 30 generates one or more output signals in in response to X-ray irradiation thereof by the X-ray generator 25, where said output signals may be processed to provide image data, also referred to herein as digital data. In some example embodiments, the sensor array 31 may generate output signals that are the aforementioned digital data and/or image data without additional processing. The digital data obtained from the sensor array 31 is recorded in the image memory 35 in a real time manner (S23). As described above, digital data can be recorded in the image memory 35 as parallel data without converting the data from parallel to serial. After the imaging is completed (S24), the rotational kinetic energy of the rotating part 23 causes a counter electromotive force in the induction coil(s) to be recovered as an electric energy, and the rotational movement is decelerated while charging the capacitor or the rechargeable battery 27 (S25). Finally, the gantry stops at a predetermined position (S26) such that the rotating part interface and the host interface are face to face with each other and configured to be electrically connected with each other, the data recorded in the image memory 35 is read from the rotating part interface through the host interface (S27), and the image is reconstructed by the operation and control unit 40-1. The data read from the rotating part interface 2-2 via the host interface 2-1 may be communicated to the control unit 40-1 (e.g., via cable 40-3). The control unit 40-1 may perform an image reconstructing process on said data. After processing, the resulting (e.g., shooting) image is caused by the control unit 40-1 to be displayed on the display monitor 40-2. In parallel, the rechargeable battery 27 is charged (S28), and then a series of sequences is completed to enter the standby state (S29). As will be described later and not shown in the flowchart, it may be also preferable to add a step in which the used rechargeable battery 27 is disconnected and an already charged rechargeable battery is mounted instead when the gantry stops at a predetermined position and returns to the next imaging step (first step of the flowchart).

Figures 10A, 10B:
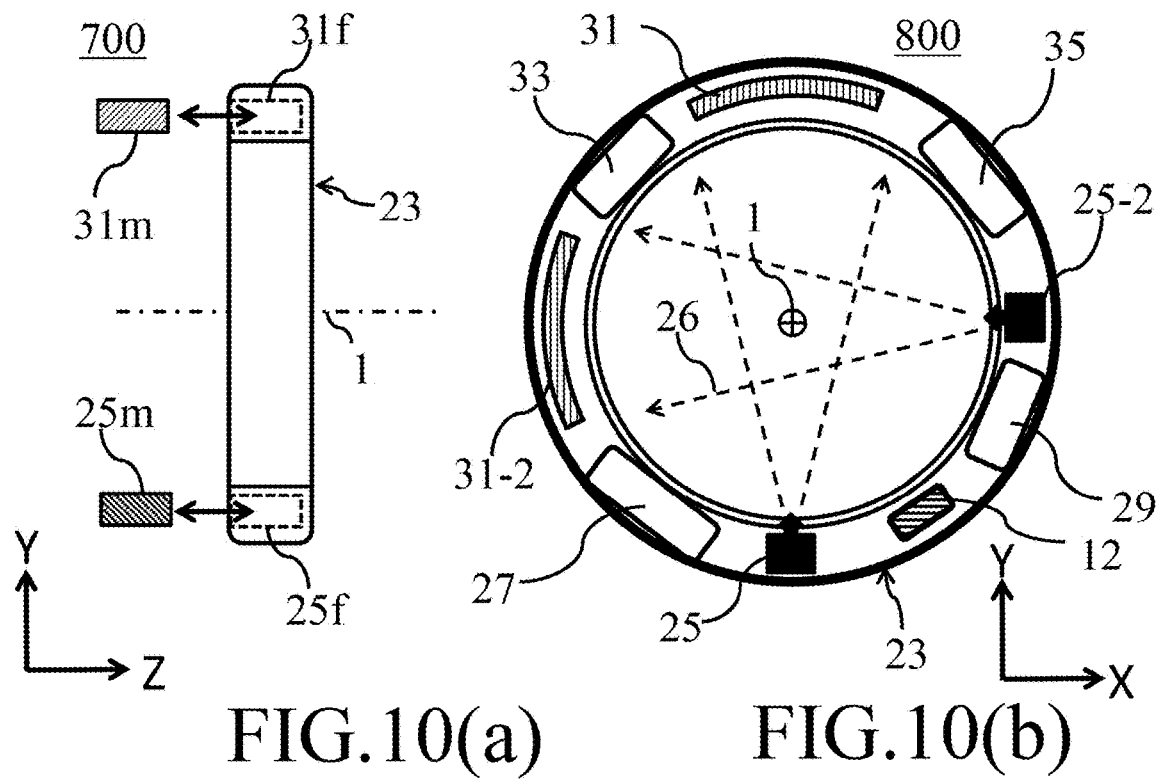
FIG. 10(a) is a diagram illustrating a cross-sectional view of the rotating part used in the CT system as seen from the X-axis direction according to at least one example embodiment.
FIG. 10(b) is a diagram illustrating a plan view seen from the Z-axis direction showing the gantry structure of the CT system according to at least one example embodiment.
Figure 10C:
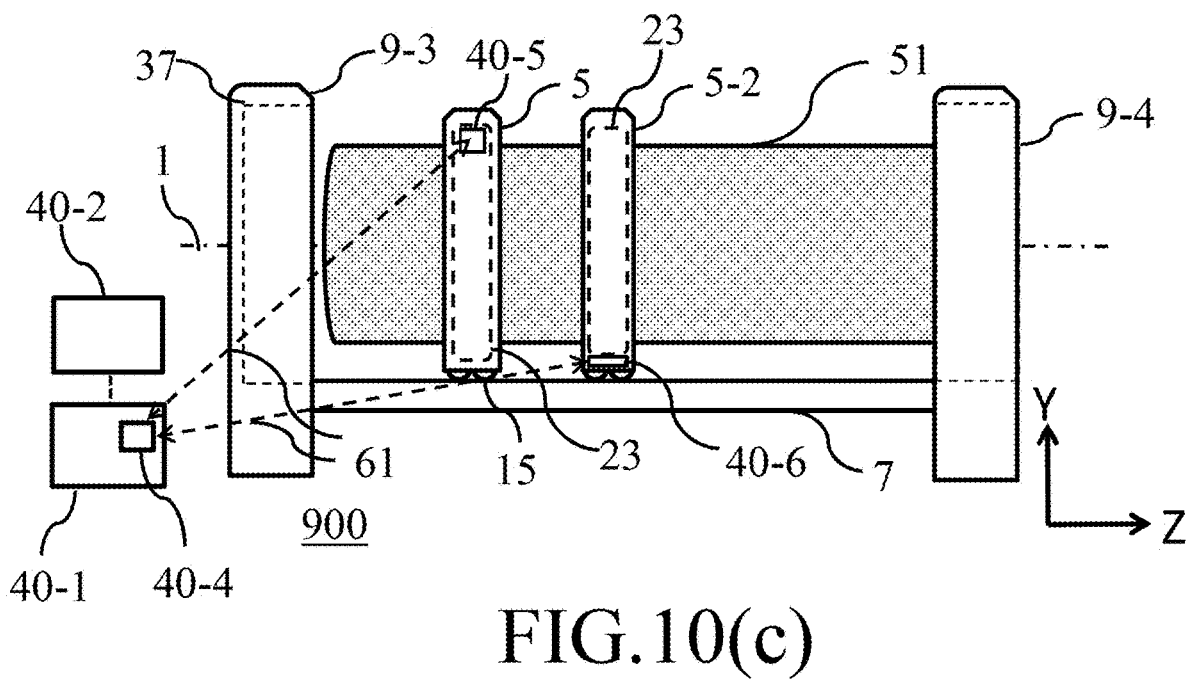
FIG. 10(c) is a diagram illustrating a side view of the CT system as seen from the X-axis direction according to at least one example embodiment.

FIG. 10(a) is a cross-sectional view seen from the X-axis direction showing the gantry portion of the CT system 700 according to at least one example embodiment. The X-ray generator 25m, which is a component incorporated in the rotating part 23, should be replaced corresponding to the frequency of use due to the deterioration of the target member, and consumption of the electron beam generating cold cathode materials or carbon nano materials in this example. Similarly, the sensor array 31m may also need to be replaced due to the radiation damage to the semiconductor components used or the humidity dependency of the laminated X-ray scintillator material. Therefore, in at least one example embodiment, the X-ray generator 25m and the sensor array 31m employs cartridge form, which is detachable from the rotation part 23. As shown in FIG. 10(a), the rotating part 23 is provided with a cartridge receiving spaces 25f and 31f (both indicated by broken line portions) into which the cartridge types X-ray generator 25m and the sensor array 31m are inserted. The X-ray generator 25m and the sensor array 31m are inserted and removed in the Z-axis or the body axis direction, and the openings for inserting or removing the cartridges are faced in the Z-axis direction. It may be suitable for the cartridge form to be used in the case having the above mentioned cradle structure (FIG. 3(a)) for example, when an old cartridge is replaced with a new cartridge kept in the cradle side. The cartridge form is not limited to the X-ray generator 25m and the sensor array 31m, but as described above (FIG. 4(a), for example), the rechargeable battery 27, or an image memory 35 according to the increase in recording capacity may have such a cartridge form.

FIG. 10(b) is a plan view showing the rotating part 23 of the CT system 800 as seen from the Z-axis direction, according to at least one example embodiment. As will be described below in detail, the energy recovery brake circuit 50 may be incorporated inside the rotating part 23. In at least one example embodiment, in addition to the image memory 35, and the rechargeable battery 27, the first X-ray generator 25 and the second X-ray generator 25-2 are provided, and a first sensor array 31 and a second sensor array 31-2 are placed on the opposite sides of these X-ray generators via the central axis 1. The sensor array 31 or the sensor array 31-2 may be arranged at positions shifted in the Z-axis direction. Further, the X-ray generator 25 and the X-ray generator 25-2 may emit X-rays at the same time or with a different timing. Furthermore, different X-ray tube voltages (or wavelengths) can be applied to the X-ray generator 25 and the X-ray generator 25-2 to perform multispectral analysis. As mentioned above, the X-ray generators 25, 25-2, the sensor arrays 31, and 31-2 may also have a cartridge form. With these configurations using the cartridge form for the main parts inside the rotating part 23, it enables not only reducing the maintenance load such as parts replacement or repair but also extending the operation time of the system. It should be also noted that extremely useful functions and effects such as versatility of imaging and inspection like the multi-spectral image analysis or these hybridizations are realized.

FIG. 10(c) is a side view of a CT system 900 as seen from the X-axis direction according to another example embodiment. Two gantries (gantry 5 and gantry 5-2) are mounted on the gantry table 7 having two cradles (9-3 and 9-4). The cradle 9-4 has a donut-shaped hollow structure so that a subject and a bed (not shown in the figure) can pass through the hollow structure. The CT system 900 enables various examinations by the multiple gantries such as a combination of X-ray CT inspection gantry and PET (positron emission tomography) inspection gantry, or combination of X-ray CT inspection gantry and near infrared diffused light imaging gantry. Further, a protective cover 51 is provided above the gantry table along the moving direction of the gantry in order to prevent the subject or the object to be examined from coming into contact with the gantry during the movement of the gantry. The plurality of gantries can be driven individually or in conjunction with each other. Preferably, a high-speed wireless communication interface may be introduced between the gantry (40-6) or the rotating part (40-5) and the operational control part (e.g., control unit 40-1), (40-4), in order to monitor output signal like a fluoroscopic image of the subject from the rotating part or the gantry while the gantry 5, 5-2 is moving in the body axis direction.

In some example embodiments, including the example embodiments shown in FIG. 10(c) but also any of the example embodiments, including the example embodiments shown in FIG. 1(a), the control unit 40-1 may include a wireless communication interface 40-4 (e.g., a 5G wireless network communication transceiver, an ad hoc wireless network communication transceiver such as a Bluetooth® transceiver, or the like), and the gantry 5 and/or a rotating part 23 of the gantry 5 may include a corresponding wireless communication interface 40-6, 40-5, etc. (e.g., each of the wireless communication interfaces may be a 5G wireless network communication transceiver, an ad hoc wireless network communication transceiver such as a Bluetooth® transceiver, or the like) As shown in FIG. 10(c), the wireless communication interface 40-4 may establish one or more wireless communication links 61 with the corresponding wireless communication interfaces 40-5, 40-6, etc. to thus establish a wireless communication link(s) between the control unit 40-1 and one or more gantries and/or rotating parts of the CT system. Data, including image data generated at a rotating part 23 and/or gantry 5, may be transmitted to the control unit 40-1 via one or more wireless communication links 61. Control signals may be generated at the control unit 40-1 and transmitted to the gantry 5 and/or rotating part 23 via one or more of the wireless communication links 61. Such control signals may include control signals to cause the gantry 5 and/or rotating part 23 to engage in movement, control signals to cause the gantry to perform an imaging operation, some combination thereof, or the like. Therefore, in at least one example embodiment, the control unit 40-1 and at least one gantry 5, 50-2 have respective wireless communication interfaces 40-4, 40-5, 40-6, etc. configured to enable, by wireless communication between the control unit 40-1 and the gantry/gantries 5, 5-2, at least one of: transmitting and receiving a control signal to control movement of the gantry 5, 5-2 in the Z-axis direction by wireless communication, or causing the gantry 5, 5-2 to perform an imaging operation.

Example embodiments having thus been described, it will be obvious that the same may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed:

1. A computed tomographic (CT) system, comprising:
   a gantry including a rotating part,
      wherein the rotating part includes
         a light source,
         a light source drive control circuit,
         a rechargeable battery, and
         a rotating part interface,
      wherein the gantry further includes, inside or outside the rotating part,
         a detector,
         a detector control and signal processing circuit configured to drive the detector and process an output signal from the detector, and
         an image memory configured to record the output signal of the detector,
      wherein the rotating part is configured to rotate around a central axis of a body axis direction;
   a gantry table, the gantry mounted on the gantry table, the gantry table including a host interface;
   a motor configured to cause the gantry to move in relation to the gantry table in the body axis direction between positions in relation to the gantry table within a gantry moving range; and
   a control unit configured to process and display image data obtained from the gantry,
   wherein the rotating part interface is configured to face the host interface, such that the rotating part interface and the host interface face each other and are configured to be electrically connected with each other, based on the gantry being at a predetermined position in relation to the gantry table within the gantry moving range.

2. The CT system of claim 1, wherein the predetermined position is an end point of the gantry moving range.

3. The CT system of claim 1, wherein the rotating part interface and the host interface are configured to face each other in a vertical direction based on the gantry being at the predetermined position.

4. The CT system of claim 1, wherein the rotating part interface and the host interface are configured to face each other in the body axis direction based on the gantry being at the predetermined position.

5. The CT system of claim 1, wherein the rotating part interface and the host interface are mechanical interfaces configured to be electrically connected based on being mechanically contacted with each other, based on the gantry being at the predetermined position, or
   contactless interfaces configured to be electrically connected in a contactless manner based on an interaction of an electromagnetic field therebetween, based on the gantry being at the predetermined position.

6. The CT system of claim 1, wherein the motor is inside the gantry.

7. The CT system of claim 1, further comprising a drive motor configured to rotate the rotating part in relation to the gantry, the drive motor being inside the gantry.

8. The CT system of claim 1, further comprising:
   a cradle above an upper portion of the gantry table in a vertical direction, the cradle being at the predetermined position in relation to the gantry table,
   wherein the cradle includes the host interface.

9. The CT system of claim 1, wherein the light source is an X-ray light source that includes an electron beam generating unit, the electron beam generating unit being composed of a carbon nanostructure material.

10. The CT system of claim 1, wherein
    the detector, the light source, the detector control and signal processing circuit, and the image memory are inside the rotating part, and
    the detector and the light source are at opposite sides of the rotating part such that the central axis is sandwiched between the detector and the light source.

11. The CT system of claim 1, wherein the detector is an electron multiplication sensor, an avalanche effect sensor, or a photon counting sensor.

12. The CT system of claim 1, wherein the control unit and the gantry have respective wireless interfaces configured to enable, by wireless communication between the control unit and the gantry,
    transmitting and receiving a control signal to control movement of the gantry in the body axis direction by wireless communication, or
    causing the gantry to perform an imaging operation.

13. The CT system of claim 1, further comprising a protective cover above the gantry table, the protective cover extending along the body axis direction.

14. The CT system of claim 1, wherein
    inside the rotating part, at least one of the light source, the detector, the rechargeable battery, or the image memory has a cartridge form including electrical contacts, and
    the rotating part has a cartridge receiving space into or from which the at least one of the light source, the detector, the rechargeable battery, or the image memory having the cartridge form is configured to be inserted or removed.

15. The CT system of claim 1, further comprising a second gantry on the gantry table.

16. The CT system of claim 1, wherein the detector includes a sensor array of sensors that are arranged over an entire inner circumference of a fixed part surrounding the rotating part inside the gantry.

17. The CT system of claim 16, wherein:
    the rotating part includes an opening configured to allow light emitted from the light source to pass therethrough in the rotating part, and
    the opening and the light source are at opposite sides of the rotating part such that the central axis is sandwiched therebetween.

18. The CT system of claim 1, further comprising:
    a plurality of induction coils;

permanent magnets; and an energy recovery brake circuit configured to convert an electromotive force in the plurality of induction coils, induced by a moment of inertia about the rotating part, into electric energy, wherein the plurality of induction coils are arranged along an annular part of the rotating part, the permanent magnets are arranged along a fixed part of the gantry surrounding the rotating part so that N poles and S poles of the permanent magnets are alternately facing the annular part of the rotating part, and the energy recovery brake circuit is in the rotating part, or the plurality of induction coils are arranged along a circumference of a fixed part inside the gantry surrounding a circumference of the rotating part, the permanent magnets are arranged along the circumference of the rotating part so that N poles and S poles of the permanent magnets are alternately facing the circumference of the fixed part, and the energy recovery brake circuit is in the fixed part.

19. A method of driving the CT system of claim 18, the method comprising:

causing the gantry to begin to move after rotational movement of the rotating part around the central axis has started;

performing an imaging operation, the imaging operation including X-ray irradiation of the detector by the light source to cause the detector to generate digital data in response to the X-ray irradiation;

recording digital data obtained from the detector in the image memory based on the X-ray irradiation;

causing a counter electromotive force in the plurality of induction coils to be recovered by the energy recovery brake circuit as electric energy being caused by rotational kinetic energy of the rotating part, such that the rotational movement is decelerated while the energy recovery brake circuit charges a capacitor or the rechargeable battery with the electric energy;

causing the gantry to stop at the predetermined position, and causing the digital data recorded in the image memory to be read from the rotating part interface through the host interface.

20. The CT system of claim 1, wherein the rotating part interface is configured to face the host interface, such that the rotating part interface and the host interface face each other and are configured to be electrically connected with each other, based on the rotating part being rotated to a particular rotational position where the rotating part interface is at a particular position to face the host interface.

* * * * *